(12) United States Patent
El Ali et al.

(10) Patent No.: US 9,845,282 B1
(45) Date of Patent: *Dec. 19, 2017

(54) PALLADIUM CATALYZED SYNTHESIS OF ESTER COMPOUNDS

(71) Applicant: KING FAHD UNIVERSITY OF PETROLEUM AND MINERALS, Dhahran (SA)

(72) Inventors: Bassam M. El Ali, Dhahran (SA); Mansur B. Ibrahim, Dhahran (SA); Rami K. Suleiman, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/643,725

(22) Filed: Jul. 7, 2017

Related U.S. Application Data

(63) Continuation of application No. 15/235,169, filed on Aug. 12, 2016, now Pat. No. 9,745,247.

(51) Int. Cl.
| | |
|---|---|
| *C07C 67/36* | (2006.01) |
| *B01J 31/18* | (2006.01) |
| *B01J 31/16* | (2006.01) |
| *C07C 51/12* | (2006.01) |
| *C07C 231/10* | (2006.01) |
| *B01J 31/06* | (2006.01) |

(52) U.S. Cl.
CPC ............... *C07C 67/36* (2013.01); *B01J 31/06* (2013.01); *B01J 31/1658* (2013.01); *B01J 31/182* (2013.01); *C07C 51/12* (2013.01); *C07C 231/10* (2013.01); *B01J 2231/49* (2013.01); *B01J 2531/824* (2013.01); *C07C 2601/16* (2017.05)

(58) Field of Classification Search
None
See application file for complete search history.

(56) References Cited

U.S. PATENT DOCUMENTS

| 3,988,358 A | 10/1976 | Heck |
|---|---|---|
| 4,374,262 A | 2/1983 | McGinnis et al. |

(Continued)

FOREIGN PATENT DOCUMENTS

| CA | 2336115 | 1/2000 |
|---|---|---|
| CN | 101456815 A | 6/2009 |
| CN | 104892547 A | 9/2015 |

OTHER PUBLICATIONS

Zheng, SZ, et al.. "NHC-Pd complex-catalyzed double carbonylation of aryl iodides with secondary amines to alpha-keto amides", Applied Organometallic Chemistry, vol. 28, No. 1, Jan. 2014, pp. 48-53 (Abstract only).

(Continued)

*Primary Examiner* — Rosalynd A Keys
*Assistant Examiner* — Amy C Bonaparte
(74) *Attorney, Agent, or Firm* — Oblon, McClelland, Maier & Neustadt, L.L.P.

(57) ABSTRACT

A catalytic process for synthesizing an ester compound, and a catalytic process for synthesizing an amide compound, wherein a solid-supported palladium catalyst is used to catalyze an alkoxycarbonylation reaction of an aryl halide to form the ester compound, or to catalyze an aminocarbonylation reaction of an aryl halide to form the amide compound. Various embodiments of each of the processes are also provided.

12 Claims, 9 Drawing Sheets

(56) References Cited

U.S. PATENT DOCUMENTS

| | | |
|---|---|---|
| 5,344,961 A | 9/1994 | Drent |
| 5,693,746 A | 12/1997 | Perry |
| 7,094,919 B2 | 8/2006 | Boaz et al. |
| 9,745,247 B1 * | 8/2017 | El Ali .................... C07C 67/36 |

OTHER PUBLICATIONS

Anna M. Trzeciak, et al., "Catalytic activity of palladium complexes, $PdCl_2$ (COD) and $PdCl_2(P(OPh)_3)_2$, in methoxycarbonylation of iodobenzene", Inorganic Chemistry Communications, vol. 6, No. 7, Jul. 2003, pp. 823-826 (Abstract only).

Chad M. Kormos, et al., "Alkoxycarbonylation of aryl iodides using gaseous carbon monoxide and pre-pressurized reaction vessels in conjuction with microwave heating", Organic & Biomolecular Chemistry, vol. 5, Issue 1, 2007, pp. 65-68 (Abstract only).

Kirill V. Nikitin, et al., "Synthesis of Aryl Esters by Pd-catalysed Carbonylation of Aryl Iodides", Mendeleev Communications, vol. 1, No. 4, 1991, pp. 129-131.

B. Aranda, et al., "Aminocarbonylation Reaction Using Palladium Complexes Containing Phosphorus-Nitrogen Ligands as Catalysts", J. Chil. Chem. Soc., vol. 58, No. 4, 2013, pp. 2136-2137.

I. P. Beletskaya, et al., "Hydroxy- and alkoxycarbonylation of aryl iodides catalyzed by polymer-supported palladium", Reac Kinet Mech Cat. vol. 99, 2010, pp. 1-4.

Yizhu Lei, et al., "Palladium supported on triphenylphosphine-functionalized porous organic polymer: an efficient heterogeneous catalyst for aminocarbonylation", Transition Met Chem, vol. 41, 2016, pp. 1-7.

Tongyu Xu, et al., "Pd-Catalyzed Chemoselective Carbonylation of Aminophenols with Iodoarenes: Alkoxycarbonylation vs Aminocarbonylation", Journal of the American Chemical Society, vol. 136, 2014, pp. 16970-16973.

Xiao-Feng Wu, et al., "Selective Palladium-Catalyzed Aminocarbonylation of Aryl Halides with CO and Ammonia", Chemistry a European Journal, vol. 16, 2010, pp. 9750-9753.

Rajendra Shivaji Mane, et al., "Silica supported palladium-phosphine as a reusable catalyst for alkoxycarbonylation and aminocarbonylation of aryl and heteroaryl iodides", RSC Advances, Royal Society of Chemistry, vol. 5, 2015, pp. 94776-94785.

Ibrahim ("A palladium-bisoxazoline supported catalyst for selective synthesis of aryl esters and aryl amides via carbonylative coupling reactions" RSC Advances, first published on Aug. 15, 2016, vol. 6, p. 78826).

Ibrahim ("Synthesis, crystal structure, and catalytic activities of new palladium(II)-bis(oxazoline) complexes" Transit Met Chem, 2016, 41, 739-749).

Hallman ("Polymer-bound bis (oxazoline) as a chiral catalyst" Tetrahedron; Asymmetry 12, 2001, p. 1475-1478).

Gruber-Woelfler ("Synthesis, catalytic activity, and leaching studies of a heterogeneous Pd-catalyst including an immobilized bis(oxazoline) ligand" Journal of Catalysis 286, 2012, p. 30-40).

* cited by examiner

PALLADIUM CATALYZED SYNTHESIS OF ESTER COMPOUNDS

CROSS-REFERENCE TO RELATED APPLICATIONS

The present application is a continuation of Ser. No. 15/235,169, now allowed, having, a filing date of Aug. 12, 2016.

STATEMENT OF FUNDING ACKNOWLEDGEMENT

This project was funded by the National Plan for Science, Technology and Innovation (MARIFAH)—King Abdulaziz City for Science and Technology—through the Science & Technology Unit at King Fahd University of Petroleum & Minerals (KFUPM), the Kingdom of Saudi Arabia, award number (14-PET2737-04).

BACKGROUND OF THE INVENTION

Technical Field

The present invention relates to a process for synthesizing ester compounds (via alkoxycarbonylation reactions) and a process for synthesizing amide compounds (via aminocarbonylation reactions) in the presence of a solid-supported palladium catalyst, Description of the Related Art The "background" description provided herein is for the purpose, of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention Palladium catalyzed carbonylation reactions of aryl halides (carbonylative coupling) in the presence of alcohol or amine nucleophiles represent major industrial processes for the production of value-added bulk and fine chemicals. It is a versatile synthetic pathway which allows the obtaining of a wide range of linear, branched and cyclic carboxylic acids and their derivatives in one step and from easily accessible starting precursors [El Ali, B. and Alper, H. *Transition metals far for synthesis: Building blocks and fine chemicals* (eds. M. Beller and C. Bolm); Wiley-VCH verlage GMBH, 2004 weinheim, Germany; Jayasree, S.; Seayad, A.; Gupte, S. P.; Chaudhari, R. V. *Catalysis Letters*, 1999, 5, 8213; Scrivanti, A.; Matteoli, U.; Beghetto, V.; Antonaroli, S.: Scarpelli, R.; Crociani, B. *J. Mol. Catal. A: Chem.*2001, 170, 51; El Ali, B.; Alper, H.; in: M. Beller, C. Bolm (Eds.), *Transition Metals for Organic Synthesis*, Vol. 1, VCH, Weinheim, 1998, 57]. The products of alkoxycarbonylation and aminocarbonylation reactions are extensively used as building blocks for various materials ranging from polymers [Claufield, M. J.; Qiao, G. G.; Solomon, D. H. *Chem. Rev.*2002, 102, 3067], light sensitive and electrically conductive materials, detergents, flavors, fragrances and various pharmaceuticals [T. W. Graham Solomons, Organic Chemistry, 11th Edition, Wiley, 2013; C. Liana Allen, Catalytic Approaches to the Synthesis of Amide Bonds, PhD Thesis, University of Bath, 2012; David Rowe, Chemistry and Technology of Flavours and Fragrances, Wiley-Blackwell, 2009; Bianchini, C.; Mantovani, G.; Meli, A.; Oberhauser, W.; Bruggeller, P. and Stampfi, T. *J. Chem. Soc., Dalton Trans.*,2001, 690].

A plethora of homogeneous palladium catalysts have been described to successfully catalyze carbonylative coupling reactions with high selectivity, activity and low catalyst loading [Fang, W. ; Deng, Q. ; Xu, M.; Tu, T., *Org. Lett.*,2013, 15, 3678-3681; Nielsen, D. U.; Taaning, R. H.; Lindhardt, A. T.; Gøgsig, T. M.; Skrydstrup, T.,*Org. Lett.*, 2011, 13, 4454-4457; Tambade, P. J.; Patil, Y. P.; Bhanushali, M. J.; Bhanage, B. M., *Synthesis*, 2008, 2347-2352; McNulty, J.; Nair, J. J.; Robertson, A.; Lei, A., *Org. Lett.*, 2007, 9, 4575-4578], However, the complete removal of the homogeneous catalyst from the cross coupling products is a tedious and costly process. This reduces the chances of industrial implementation of most homogeneous palladium catalysts since metal contamination in the final products is highly regulated by the industries [Polshettiwar, V.; Len, C.; Fihri, A. *Coord. Chem. Rev.*2009, 253, 2599].

A suitable method for overcoming the separation problem is by immobilizing the homogeneous catalyst on a solid support [Gruber-Woelfler, H.; Radaschitz , P. F.; Feenstra, P. W.; Haas, W.; Khinas, J. G. *J. Catal.*2012, 286, 30]. Other than easy removal from the coupling products, the immobilized catalyst can be also effectively recycled and re-used [Hallamn, K.; Moberg, C. *Tetrahedron: Asymmetry*,2001, 12, 1475]. The ability to separate and reuse the supported catalyst makes it more viable alternative especially from economical point of view. Taking into consideration the substantial advantages of supported catalysts over the homogeneous catalysts, the interest towards the immobilization of palladium catalysts has been increasing rapidly [Lei, Y.; Wu, L.; Zhang, X.; Mei, H.; Yanlong Gu, Y.; Li; G., *J. Mol. Catal.*, 2015, 398, 164-169; Mane, R. S.; Sasaki, T.; Bhanage, B. M., *RSC Adv.*,2015, 5, 94776-94785; Beletskaya, I. P.; Ganina, O. G.; *Reac. Kinet. Mech. Cat.*,2010, 99, 1-4; Khedkar, M. V; Sasaki, T.; Bhanage, B. M.,*ACS Catal.*, 2013, 3, 287-293; Dang, T. T.; Zhu, Y.; Ngiam, J. S. Y.; Ghosh, S. C.; Chen, Seayad, A. M. *ACS Catal.*,2013, 3, 1406-1410]. Although several supported palladium catalysts have been reported, the application of supported palladium-bis(oxazolines) catalysts in carbonylative coupling reactions has never been explored [Ibrahim, M. B.; El Ali, B.; Fettouhi, M.; Ouabab, L. *Appl. Organometal. Chem.*, 2015, 29, 400.; Ibrahim, M. B.; Hussain, S. M.; Fazal A.; Fettouhi, M.; El Ali, B. *J. Coord. Chem*, 2015, 68:3, 432; Hussein, S. M.; Ibrahim, M. B. Fazal, A.; Suleiman, R.; Fettouhi, M.; El Ali, B. *Polyhedron*,2014, 70, 39]. Therefore, the process of synthesizing ester and amide compounds via alkoxycarbonylation and aminocarbonylation reactions of aryl halides is discussed, wherein a palladium-bis(oxazoline) complex supported on Merrifield's resin is used as a reaction catalyst. Further, the catalytic activity and recycling ability of the catalyst in alkoxycarbonylation and, aminocarbonylation reactions of aryl halides have been studied.

In view of the forgoing, one objective of the present invention is a process for synthesizing ester compounds (via alkoxycarbonylation reactions) and a process for synthesizing amide compounds (via aminocarbonylation reactions) in the presence of a solid-supported palladium catalyst.

BRIEF SUMMARY OF THE INVENTION

According to a first aspect the present disclosure relates to a process for synthesizing an aryl ester compound, involving i) mixing an aryl halide compound, an alcohol, a base, and a catalyst in a reaction chamber, ii) pressurizing the reaction chamber with carbon monoxide, iii) heating the reaction chamber to react the aryl halide compound with carbon monoxide and the alcohol in the presence of the catalyst via an alkoxycarbonylation reaction to form the aryl ester compound, wherein the catalyst has a structure of formula (I):

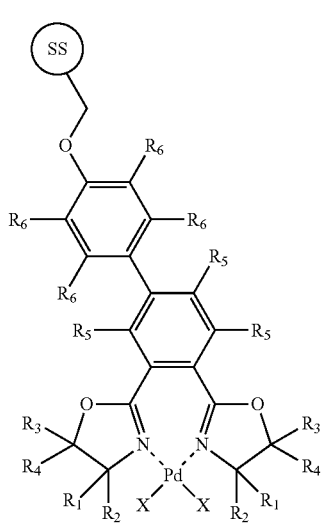

(I)

wherein $R_1$, $R_2$, $R_3$, $R_4$, $R_5$, and $R_6$ are independently a hydrogen, an optionally substituted alkyl, an optionally substituted cycloalkyl, an optionally substituted cycloalkylalkyl, optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted aryl halide, an optionally substituted arylolefin, an optionally substituted arylalkylcarboxylic acid, an optionally substituted benzyl, or an optionally substituted vinyl; SS is a solid support; and X is selected from the group consisting of Cl, F, Br, I, OAc, and OTf.

In one embodiment, the catalyst has a structure of formula (II):

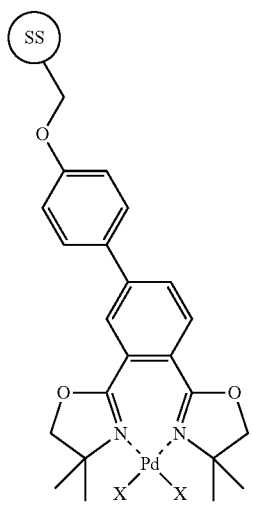

(II)

wherein SS is a solid support, and X is selected from the group consisting of Cl, F, Br, I, OAc, and OTf.

In one embodiment, the catalyst has a structure of formula (II):

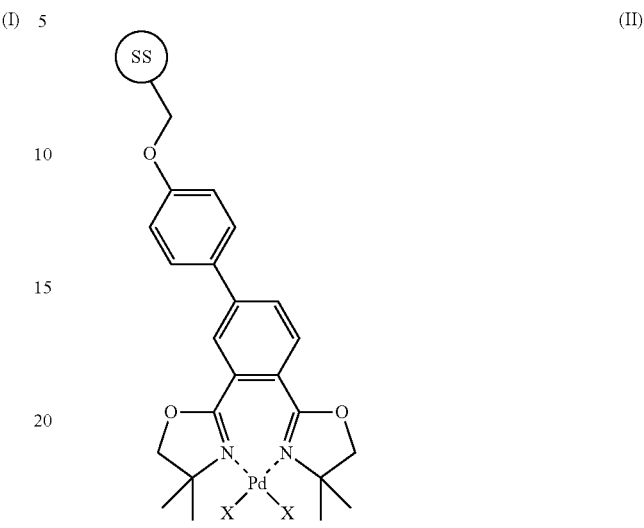

(II)

wherein SS is a Merrifield resin, and X is selected from the group consisting of Cl, F, Br, I, OAc, and OTf.

In one embodiment, the catalyst has a structure of formula (III):

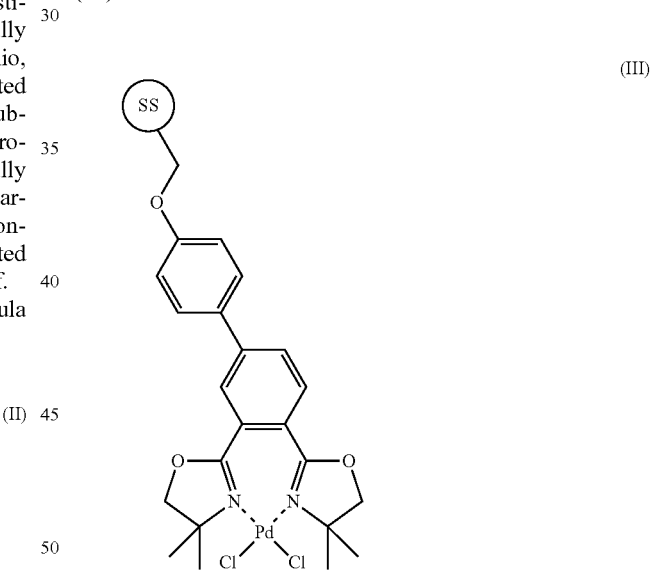

(III)

wherein SS is a Merrifield resin.

In one embodiment, the catalyst is in the form of spherical particles having an average diameter within the range of 1-50 nm.

In one embodiment, the process for synthesizing an aryl ester compound further involves i) separating the catalyst from the aryl ester compound, ii) recycling the catalyst, wherein the catalyst loses less than 5 wt % of the palladium metal after at least 10 cycles.

In one embodiment, a turnover number of the catalyst in the alkoxycarbonylation reaction after at least 10 cycles is within the range of 1,800 to 10,000.

In one embodiment, a turnover frequency of the catalyst in the alkoxycarbonylation reaction after at least 10 cycles is within the range of 300-2,000 per hour.

In one embodiment, the alkoxycarbonylation reaction is conducted at a temperature in the range 25-200° C., and a pressure in the range of 80-150 psi.

In one embodiment, a formation yield of the aryl ester compound is at least 80%, with the formation yield being relative to an initial molar weight of the aryl halide compound.

In one embodiment, the base is at least one selected from the group consisting of an alkali metal hydroxide, an alkali metal carbonate, and an amine.

In one embodiment, the aryl halide compound is a limiting reactant in the alkoxycarbonylation reaction.

According to a second aspect the present disclosure relates to a process for synthesizing an amide compound, involving i) mixing an aryl halide compound, an amine, a base, an organic solvent, and a catalyst in a reaction chamber, ii) pressurizing the reaction chamber with carbon monoxide, heating the reaction chamber to react the aryl halide compound with carbon monoxide and the amine in the presence of the catalyst via an aminocarbonylation reaction to form the amide compound, wherein the catalyst has a structure of formula (I):

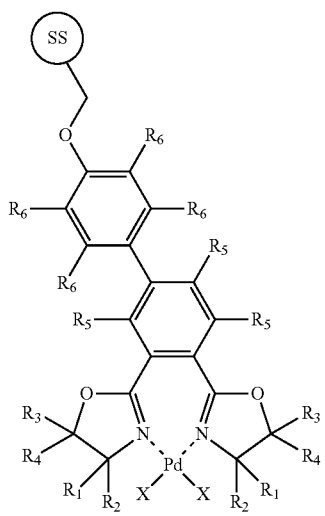

(I)

wherein $R_1$, $R_2$, $R_3$, $R_4$, $R_5$, and $R_6$ are independently a hydrogen, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkythio, an optionally substituted alkanoyl, an optionally substituted aroyl, an optionally substituted aralkyl, an optionally substituted heteroarylcarbonyl, an optionally substituted hydrocarbyl, an optionally substituted aryl halide, an optionally substituted arylolefin, an optionally substituted arylalkylcarboxylic acid, an optionally substituted benzyl, or an optionally substituted vinyl; SS is a solid support; and X is selected from the group consisting of Cl, F, Br, I, OAc, and OTf.

In one embodiment, the catalyst has a structure of formula (II):

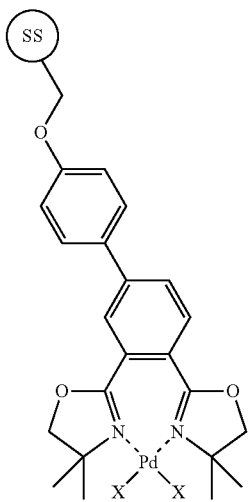

(II)

wherein SS is a solid support, and X is selected from the group consisting of Cl, F, Br, I, OAc, and OTf;

In one embodiment, the catalyst has a structure of formula (II):

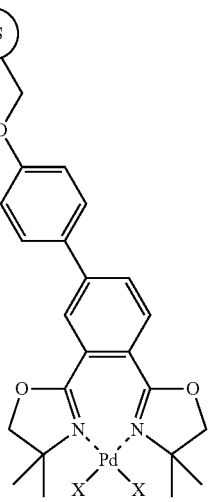

(II)

wherein SS is a Merrifield resin, and X is selected from the group consisting of Cl, F, Br, I, OAc, and OTf.

In one embodiment, the catalyst has a structure of formula (III):

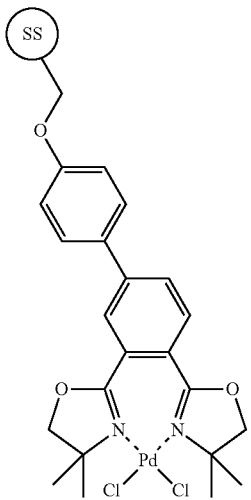

(III)

wherein SS is a Merrifield resin.

In one embodiment, the aminocarbonylation reaction is conducted at a temperature in the range 25-200° C. and a pressure in the range of 100-250 psi.

In one embodiment, the amine comprises one or more of a primary amine and a secondary amine.

According to a third aspect the present disclosure relates to a process for synthesizing a carboxylic acid compound, involving i) mixing an aryl halide compound, water, a base, and a catalyst in a reaction chamber, ii) to pressurizing the reaction chamber with carbon monoxide, iii) heating the reaction chamber to react the aryl halide compound with carbon monoxide and water in the presence of the catalyst via a hydroxycarbonylation reaction to form the carboxylic acid compound, wherein the catalyst has a structure of formula (I):

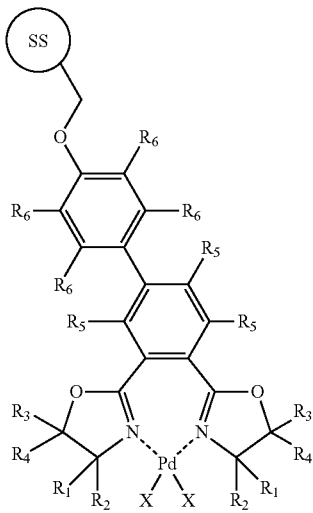

(I)

wherein $R_1$, $R_2$, $R_3$, $R_4$, $R_5$, and $R_6$ are independently a hydrogen, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted aryl halide, an optionally substituted arylolefin, an optionally substituted arylalkylcarboxylic acid, an optionally substituted benzyl, or an optionally substituted vinyl; SS is a solid support; and X is selected from the group consisting of Cl, F, Br, I, OAc, and OTf.

In one embodiment, the catalyst has a structure of formula (III):

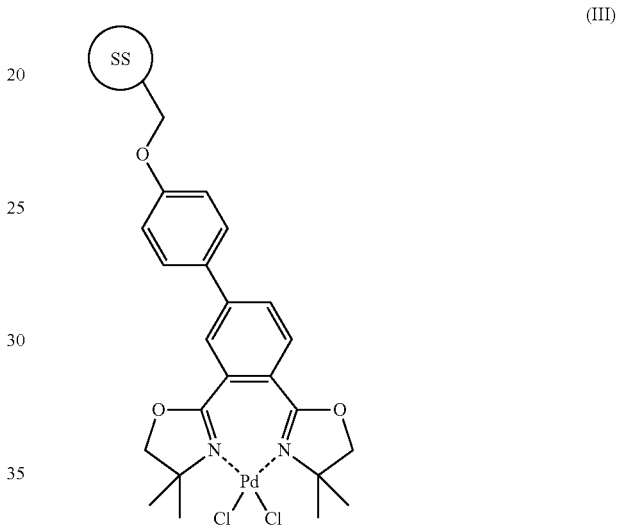

(III)

wherein SS is a Merrifield resin.

The foregoing paragraphs have been provided by way of general introduction, and are not intended, to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
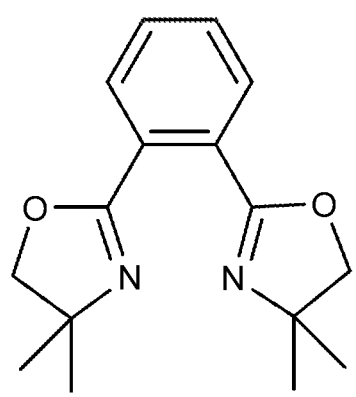
FIG. 1 is a chemical structure of a catalyst ligand precursor (i.e. BOX-1).

Referring now to the drawings, wherein like reference numerals designate identical corresponding parts throughout the several views.

According to a first aspect the present disclosure relates to a process for synthesizing an aryl ester compound via an alkoxycarbonylation reaction, involving mixing an aryl halide compound, an alcohol, a base, and a catalyst in a reaction chamber.

The aryl ester compound has a structure of formula (A):

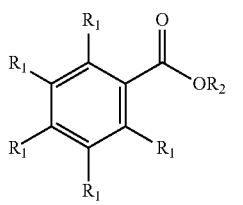

(A)

wherein $R_1$ and $R_2$ are independently an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted benzyl, or an optionally substituted vinyl.

Organic substituents as used herein are described in detail in the "description of to organic substituents" section of this disclosure.

The aryl halide compound has a structure of formula (B):

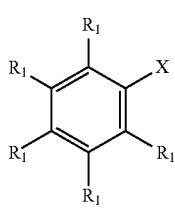

(B)

wherein $R_1$ is independently a hydrogen, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted benzyl, or an optionally substituted vinyl. Further, X is a halogen selected from the group consisting of fluorine, chlorine, bromine, and iodine.

The alcohol as used in this process act as a nucleophile compound in the alkoxycarbonylation reaction. In a preferred embodiment, the alcohol also acts as a solvent, wherein the aryl halide and the base are dissolved within. Accordingly, the alcohol may be present in excess in the alkoxycarbonylation reaction (i.e. the reactant are not in stoichiometric ratio, and the aryl halide compound is a limiting reactant). In one embodiment, the alcohol is in a solid form (e.g. phenol), and an organic solvent is used to dissolve the alcohol, the base, and it aryl halide compound. The organic solvent may be a liquid ketone, more preferably liquid dialkyl ketone having six carbon atoms molecule, and most preferably methyl isobutyl ketone. Examples of the organic solvents may include, but not limited to dimethyl formamide, ethers, glycol ethers, acetamide, dimethyl acetamide, dimethyl sulfoxide, dioxane, tetrahydrofuran, acetonitrile, an alcohol, such as methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol,3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol, and combinations thereof. Preferably, the organic solvent is acetonitrile.

The alcohol may have an aliphatic (e.g. primary, secondary, or tertiary), a cycloaliphatic, or an aromatic structure. The alcohol has a structure of formula (C):

$$R_1-OH \qquad (C)$$

wherein $R_1$ is an optionally substituted alkyl an optionally substituted cycloalkyl an optionally substituted cycloalkylalkyl, an optionally substituted arylalkyl, an optionally substituted heteroaryl, an optionally substituted an optionally substitutes heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted arylolefin, an optionally substituted arylalkylcarboxylic acid, an optionally substituted benzyl, or an optionally substituted vinyl.

The, presence of a base is often important for a palladium-catalyzed alkoxycarbonylation reaction in order to neutralize the hydrogen halide produced as the byproduct of the reaction. The base may be an alkali metal hydroxide, for example, LiOH KOH, and NaOH, an alkali metal carbonate, for example. $Li_2CO_3$, $K_2CO_3$, and $Na_2CO_3$, or an amine such as $C_4$-$C_9$ trialkyl amine (preferably trimethylamine), piperidine, and diethylamine. Among these potassium hydroxide may be a preferred base for the alkoxycarbonylation reaction using the catalyst. A molar ratio of the base to the aryl halide compound may range from 1:1 to 8:1, preferably 1:1 to 5:1, more preferably 2:1 to 4:1. Preferably, the molar ratio ranges from 1:1 to 3:1, preferably 1.5:1 to 2.5:1.

The catalyst is a palladium complex having a structure of formula (I):

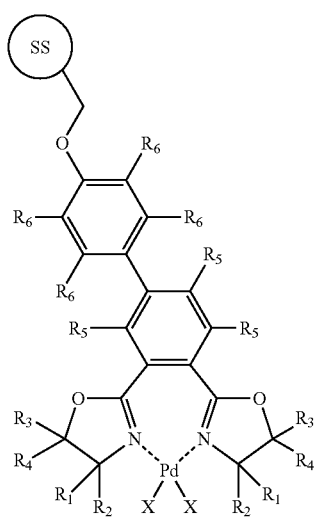

(I)

wherein $R_1$, $R_2$, $R_3$, $R_4$, $R_5$, and $R_6$ are independently a hydrogen, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted aryl halide, an optionally substituted arylolefin, an optionally substituted arylalkylcarboxylic acid, an optionally substituted benzyl, or an optionally substituted vinyl; SS is a solid support; and X is selected from the group consisting of chlorine, fluorine, bromine, iodine, acetoxy (or OAc), and trifluoromethanesulfonate (or triflate, or OTf).

In some embodiments, when $R_1$ and $R_2$ (or $R_3$ and $R_4$) are different, and either $R_1$ or $R_2$ (or $R_3$ and $R_4$) is a hydrogen atom, a ligand is chiral and has two enantiomers. Either enantiomer may be employed in the present disclosure. As used herein, the term "ligand" refers to an, organic molecule comprising a biphenyl moiety, and two oxazoline groups bound separately to the biphenyl moiety via a C—C bond and arranged ortho to one another. In one embodiment, the ligand is attached to a solid support from the biphenyl moiety via a C—O—C bond. The ligand chelate a palladium metal by nitrogen atoms present in the oxazoline groups. The ligand may chelate a metal selected from the group consisting of nickel, platinum, rhodium, iron, gold, silver, ruthenium and iridium. In one embodiment, $R_1$ and $R_2$ (or $R_3$ and $R_4$) may not be an amino, an alkylamino, an arylamino, a N-monosubstituted amino, a N,N-disubstituted amino, a thiol or an optionally substituted thioalkoxyl. These groups contain nucleophilic atoms that may poison the catalyst. As used herein, "poisoning" refers to the nucleophilic atom(s) coordinating strongly to the palladium metal and thereby reducing the effectiveness of the catalyst.

In a preferred embodiment, the catalyst is a palladium complex having a structure of formula (II):

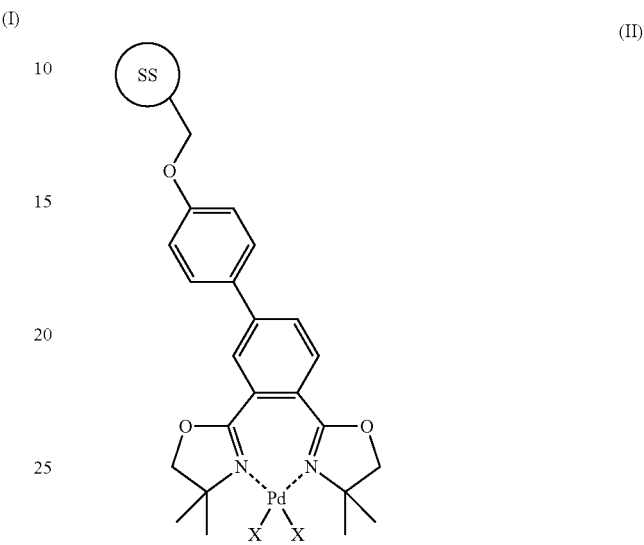

(II)

wherein SS is a solid support, and X is selected from the group consisting of chlorine, fluorine, bromine, iodine, acetoxy (or OAc), and trifluoromethanesulfonate (or triflate, or OTf). The catalyst can be immobilized by covalent coupling to a grafted or a functionalized polystyrene support. Examples of the functionalized polystyrene support include Wang resin, Argogel resin, Merrifield resin, Tentagel resin, Polyamine resins, etc. The catalyst may also be immobilized by covalent coupling to a grafted or a functionalized polymer support, wherein the functionalized polymer support is at least one selected from the group consisting of polyolefins, polyacrylates, polymethacrylates, and copolymers thereof.

In a preferred embodiment, the solid support is a Merrifield resin. Merrifield resin is a polystyrene resin based on a copolymer of styrene and chloromethyl styrene. In addition this polymer may also be crosslinked with divinyl benzene, wherein a degree of crosslinking is within the range of 1-5%, preferably 1-2%, Merrifield resin may be present in the form of spherical beads having a diameter within the range of 0.01-0.5 mm, preferably 0.01-0.15 mm, more preferably 0.05-0.15 mm.

However, the catalysts may be immobilized by covalent coupling through a silicon or siloxane containing-linker to a porous or nonporous solid support, such as silica, alumina, titania, kieselguhr, diatomaceous earth, bentonite, clay, zirconia, magnesia, zeolites, carbon black, activated carbon, graphite, fluoridated carbon, organic polymers, metals, metal alloys, and combinations thereof Furthermore, the catalyst may be immobilized by Lewis acid—Lewis base interactions, or binding to any of the above solid supports, preferably alumina or silica, without covalent coupling.

In the most preferred embodiment, the catalyst is a palladium complex having a structure of formula (III):

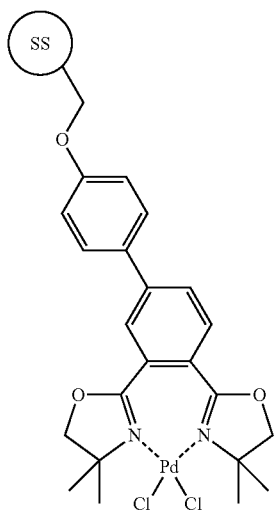

(III)

wherein SS is a Merrifield resin.

In one embodiment, the catalyst is in the form of spherical particles having an average diameter within the range of 1-50 nm, preferably 5-50 nm, more preferably 5-20 nm.

Reaction chamber refers to a pressure chamber used to carry out reactions and processes that require elevated temperature and pressure different than ambient pressure (i.e. 1 atm) and temperature (i.e. about 25° C). The reaction chamber may be made of glass, metal, metal alloy (e.g. stainless steel, nickel steel, chromium steel, aluminum, aluminum alloy, copper and copper alloys, titanium, etc.), or a combination thereof. Preferably, the reaction chamber is a stainless steel autoclave with a glass liner that is configured to bear a pressure up to 150 psi, preferably up to 200 psi, more preferably up to 250 psi. The reaction chamber may be a hollow tube, a pipe, a duct, etc. The reaction chamber may have, various geometries including spherical, conical, pyramidal, rectangular, or cubical geometries, although, the preferred geometry is cylindrical. In one embodiment, the reaction chamber has a volume in the range of 1-10,000 L, preferably 100-1,000 L, more preferably 500-1,000 L. For small scale reactions, the reaction chamber may have a volume in the range of 1-1,000 mL, preferably 10-1,000 mL, more preferably 10-500 mL.

A reaction mixture comprising the aryl halide compound, the base, the alcohol, and the catalyst is produced in the reaction chamber, wherein a molar ratio of the aryl halide compound to the base is in the range of 1:1 to 1:5, preferably 1:1 to 1:3, more preferably 1:1.5 to 1:2.5. A molar ratio of the aryl halide compound to the catalyst may be in the range of 1:0.001 to 1:0.1, preferably 1:0.005 to 1:0.01, more preferably 1:0.005, wherein the molar weight of the catalyst is measured based on the palladium metal. The alcohol may preferably be present in excess in the alkoxycarbonylation reaction. For example, a volume fraction of the alcohol in the reaction mixture may be at least 0.5, preferably at least 0.6, more preferably at least 0.7, with volume fraction being relative to the total volume of the reaction mixture. For example, in one embodiment, a reaction mixture is prepared by mixing 0.005 mmol of the catalyst, 1.0 mmol of iodobenzene, 2.0 mmol of KOH, and 5.0 mL of alcohol.

The reaction mixture is preferably a heterogeneous liquid solution, wherein the catalyst is in the form of solid particles that are suspended in the reaction mixture. In one embodiment, catalyst particles are dispersed within the reaction mixture, and may further be filtered and recycled at the end of the alkoxycarbonylation reaction. To facilitate filtering and recycling processes, the catalyst particles may be placed in a bag and immersed in the reaction mixture, similar to the method of using a teabag for making instant tea. The reaction mixture is preferably mixed at room temperature (i.e. 25° C.), or else it may be mixed at an elevated temperature (e.g. up to 40° C., or up to 60° C., but no more than 100° C.).

In one embodiment, the reaction mixture is preferably mixed in a centrifugal mixer with a rotational speed of at least 500 rpm, preferably at least 800 rpm, more preferably at least 1000 rpm, even though it can also be mixed with a spatula. In one embodiment, the reaction mixture is sonicated during the mixing.

The process for synthesizing the aryl ester compound further involves pressurizing the reaction chamber with carbon monoxide. The reaction chamber may be pressurized and vented at least three times, preferably at least five times with CO to ensure a volume fraction of other gaseous substances (e.g. nitrogen, oxygen, carbon dioxide, water vapor, etc.) is less than 0.001, preferably less than 0.0005, more preferably less than 0.0001. At this point, the reaction chamber can be pressurized with carbon monoxide to a pressure within the range of 80-150 psi, preferably 100-150 psi, more preferably at least 120-150 psi.

The process for synthesizing the aryl ester compound further involves heating the reaction chamber to react the aryl halide compound with carbon monoxide and the alcohol in the presence of the catalyst via the alkoxycarbonylation reaction to form the aryl ester compound. In one embodiment, the alkoxycarbonylation reaction is performed at a temperature in the range 25-200° C., preferably 80-120° C., even more preferably about 100° C. An external heat source, such as a water bath or an oil bath, an oven, or a heating mantle, may be employed to heat the reaction mixture. In a preferred embodiment, the external heat source is a thermostatted thermocirculator. A duration of the reaction may range from 0.5-10 hours, preferably 2-6 hours, more preferably about 3 hours. The reaction may preferably be stirred throughout the duration of the reaction by employing a magnetic stirrer or an overhead stirrer. In another embodiment, the reaction mixture is left to stand (i.e. not stirred). The progress of the alkoxycarbonylation reaction may be monitored by methods known to those skilled in the art, such as thin layer chromatography, gas chromatography, nuclear magnetic resonance, infrared spectroscopy, and high pressure liquid chromatography combined with ultraviolet detection or mass spectroscopy.

At the completion of the alkoxycarbonylation reaction, the reaction mixture may be cooled down to room temperature, and a remaining carbon monoxide may be vented. The catalyst is separated from a product mixture, for example, by filtering or sieving, and may further be recycled after being washed and dried. The product mixture may further be purified using methods that are well-known to those skilled in the art. In a preferred embodiment, a concentration of the palladium metal in the product mixture is less than 10 ppb, preferably less than 5 ppb.

In one embodiment, a formation yield of the aryl ester compound (and its isomeric compounds) is at least 80%, preferably at least 90%, more preferably at least 95%, with the formation yield being relative to an initial molar weight of the aryl halide compound.

In one embodiment, the process for synthesizing the aryl ester compound further involves separating the catalyst from the aryl ester compound, followed by recycling the catalyst. Separating the catalyst may be performed by using a microfilter or a paper filter. In one embodiment, the catalyst is placed in a bag and the bag is immersed in the reaction mixture. Accordingly, the catalyst particles remain in the bag until the alkoxycarbonylation reaction is completed.

Recycling the catalyst as used herein refers to a process whereby the catalyst is first washed by an organic solvent, and then dried. Exemplary organic solvents for washing the catalyst may include, but are not limited to methanol, acetone, ethanol, tetrahydrofuran, acetonitrile, dichloromethane, ether, glycol ether, acetamide, dimethyl acetamide, dimethyl sulfoxide, or any combination thereof. The catalyst may be dried in vacuum, and/or heat, for example, the catalyst may be dried in a vacuum oven. Dried catalyst may be stored in a desiccator until the next run.

In one embodiment, the catalyst is recycled for at least 10 times, preferably at least 15 times, more preferably at least 20 times, even more preferably at least 30 times. The catalyst may lose less than 1 wt %, preferably less than 0.5 wt %, more preferably less than 0.1 wt % of the palladium metal (i.e. an initial palladium metal present in the catalyst) after at least 10 cycles, preferably at least 15 cycles, more preferably at least 20 cycles. In a preferred embodiment, a concentration of the palladium metal in the product mixture is less than 10 ppb, preferably less than 5 ppb, more preferably less than 2 ppb, after at least 10 cycles, preferably at least 15 cycles, more preferably at least 20 cycles.

In one embodiment, a turnover number of the catalyst in the alkoxycarbonylation reaction after at least 10 cycles, preferably at least 15 cycles, more preferably at least 20 cycles is within the range of 1,800 to 10,000, preferably 1,800 to 5,000, more preferably 1,800 to 3,000, even more preferably about 1,850. The turnover number of the catalyst refers to a maximum number of the alkoxycarbonylation reaction per second that a single catalytic site will execute for a given concentration of the catalyst.

In one embodiment, a turnover frequency of the catalyst in the alkoxycarbonylation reaction after at least 10 cycles, preferably at least 15 cycles, more preferably at least 20 cycles is within the range of 300-2,000 per hour, preferably 300-1,000 per hour, more preferably 300-500 per hour, even more preferably about 320 per hour. The turnover frequency of the catalyst is defined as a maximum number of revolutions of the catalytic cycle per unit time.

According to a second aspect the present disclosure relates to a process for synthesizing an amide compound via an aminocarbonylation reaction, involving mixing an aryl halide compound, an amine, a base, an organic solvent, and a catalyst in a reaction chamber.

The amide compound has a structure of formula (D) or formula (E):

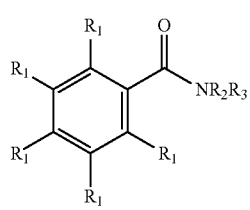

(D)

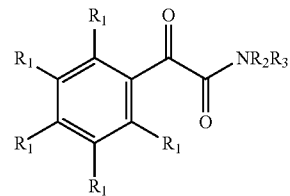

(E)

wherein $R_1$, $R_2$, and $R_3$ are independently an optionally substituted alkyl, an optionally substituted cycloalkyl, an optionally substituted cycloalkylalkyl, an optionally substituted alylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted benzyl, or an optionally substituted vinyl.

Organic substituents are described in detail in the "description of organic substituents" section of this disclosure.

The amine acts as a nucleophile compound in the aminocarbonylation reaction. The amine used in the aminocarbonylation reaction may comprise one or more of a primary amine and/or a secondary amine, and has a structure of formula (F) or formula (G):

$$R_1R_2\text{—NH} \quad (F)$$

$$R_1R_2\text{—NH}_2 \quad (G)$$

wherein $R_1$ and $R_2$ are independently an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted benzyl, or an optionally substituted vinyl.

The organic solvent may be a liquid ketone, more preferably liquid dialkyl ketone having six carbon atoms in the molecule, and most preferably methyl isobutyl ketone. Examples of the organic solvents may include, but not limited to dimethyl formamide, ethers, glycol ethers, acetamide, dimethyl acetamide, dimethyl sulfoxide, dioxane, tetrahydrofuran, acetonitrile, an alcohol, such as methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol,3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol, and combinations thereof Preferably, the organic solvent is acetonitrile.

Each of the aryl halide compound, the base, and the catalyst is similar to the ones used according to the first aspect (the alkoxycarbonylation reaction), therefore, descriptions of each compound is mentioned previously. Further, description of the reaction chamber is similar to that of the one presented in the first aspect.

A reaction mixture comprising the aryl halide compound, the base, the amine, the organic solvent and the catalyst is produced in the reaction chamber wherein a molar ratio of the aryl halide compound to the base is in the range of 1:1 to 1:5, preferably 1:1 to 1:4, more preferably 1:2.5 to 1:3.5. In addition, a molar ratio of the aryl halide compound to the amine is in the range of 1:1 to 1:5, preferably 1:1 to 1:3, more preferably 1:1.5 to 1:2.5. Furthermore, a molar ratio of the aryl halide compound to the catalyst may be in the range of 1:0.001 to 1:0.1, preferably 1:0.005 to 1:0.01, more preferably 1:0.005, wherein the molar weight of the catalyst is measured based on the palladium metal. The organic solvent may be present in excess in the aminocarbonylation reaction. For example, a volume fraction of the organic solvent in the reaction mixture may be at least 0.5, preferably at least 0.6, more preferably at least 0.7, with volume fraction being relative to the total volume of the reaction mixture. For example, in one embodiment, a reaction mixture is prepared by mixing 0.005 mmol of the catalyst, 1.0 mmol of iodobenzene, 2.0 mmol of amine, 3.0 mmol of triethylamine, and 5.0 mL of acetonitrile.

The reaction mixture is preferably a heterogeneous liquid solution, wherein the catalyst is in the form of solid particles that are suspended in the reaction mixture. In one embodiment, catalyst particles are dispersed within the reaction mixture, and may further be filtered and recycled at the end of the aminocarbonylation reaction. The reaction mixture is preferably mixed at room temperature (i.e. 25° C.), or else it may be mixed at an elevated temperature (e.g. up to 40° C., or up to 60° C., but no more than 100° C.). In one embodiment, the reaction mixture is preferably mixed in a centrifugal mixer with a rotational speed of at least 500 rpm, preferably at least 800 rpm, more preferably at least 1000 rpm, even though it can also be mixed with a spatula. in one embodiment, the reaction mixture is sonicated during the mixing.

The process for synthesizing the amide compound further involves pressurizing the reaction chamber with carbon monoxide. Similar to the pressurizing step in the alkoxycarbonylation reaction, the reaction chamber may be pressurizing and vented at least three times, preferably at least five times with CO to ensure a volume fraction of other gaseous substances (e.g. nitrogen, oxygen, carbon dioxide, water vapor, etc.) is less than 0.001, preferably less than 0.0005, more preferably less than 0.0001. At this point, the reaction chamber can be pressurized with carbon monoxide to a pressure within the range of 100-250 psi, preferably 150-250 psi, more preferably about 200 psi.

The process for synthesizing the amide compound further involves heating the reaction chamber to react the aryl halide compound with carbon monoxide and the amine the presence of the catalyst via an aminocarbonylation reaction to form the amide compound in the product mixture.

In one embodiment, the aminocarbonylation reaction is performed at a temperature in the range 25-200° C., preferably 100-150° C., even more preferably about 120° C. An external heat source, such as a water bath or an oil bath, an oven, or a heating mantle, may he employed to heat the reaction mixture. A duration of the reaction may range from 0.5-10 hours, preferably 4-10 hours, more preferably about 6 hours. The reaction may preferably be stirred throughout the, duration of the reaction by employing a magnetic stirrer or an overhead stirrer. In another embodiment, the reaction mixture is left to stand (i.e. not stirred).

In one embodiment, the process for synthesizing the amide compound further involves separating the catalyst from the product mixture, followed by recycling the catalyst. These optional processing steps are similar to the separating, and the recycling steps of the alkoxycarbonylation reaction, as described previously.

In one embodiment, a formation yield of the amide compound (and its isomeric compounds) is at least 80%, preferably at least 90%, more preferably at least 95%, with the formation yield being relative to an initial molar weight of the aryl halide compound.

In a preferred embodiment, a concentration of the palladium metal in the product mixture is less than 200 ppb, preferably less than 190 ppb, more preferably less than 150 ppb. In one embodiment, the catalyst is recycled for at least 5 times, preferably at least 7 times, more preferably at least 10 times. The catalyst may lose less than 5 wt %, preferably less than 4 wt %, more preferably less than 3.5 wt % of the palladium metal (i.e. an initial palladium metal present in the catalyst) after at least 5 cycles, preferably at least 7 cycles, more preferably at least 10 cycles. In a preferred embodiment, a concentration of the palladium metal in the product mixture is less than 300 ppb, preferably less than 250 ppb, more preferably less than 200 ppb, after at least 5 cycles, preferably at least 7 cycles, more preferably at least 10 cycles.

In one embodiment, a turnover number of the catalyst in the aminocarbonylation reaction after at least 5 cycles, preferably at least 7 cycles, more preferably at least 10 cycles is within the range of 1,800 to 10,000, preferably 1,800 to 5,000, more preferably 1,800 to 3,000, even more preferably about 1,850.

In one embodiment, a turnover frequency of the catalyst in the aminocarbonylation reaction after at least 5 cycles, preferably at least 7 cycles, more preferably at least 10 cycles is within the range of 300-2,000 per hour, preferably 300-1,000 per hour, more preferably 300-500 per hour, even more preferably about 320 per hour.

According to a third aspect the present disclosure relates to a process for synthesizing a carboxylic acid compound via a hydroxycarbonylation reaction, involving mixing an aryl halide compound, water, a base, and a catalyst in a reaction chamber.

The carboxylic acid compound has a structure of formula (H):

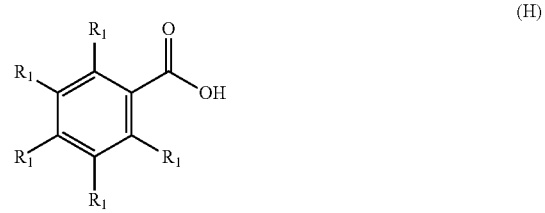

(H)

wherein $R_1$ is independently an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted benzyl, an optionally substituted vinyl.

Descriptions of the aryl halide compound, the base, the catalyst, and the reaction chamber have been mentioned previously in the first aspect.

A reaction mixture comprising the aryl halide compound, the base, water, and the catalyst is produced in the reaction chamber, wherein a molar ratio of the aryl halide compound to the base is in the range of 1:1 to 1:5, preferably 1:1 to 1:3, more preferably 1:1.5 to 1:2.5. A molar ratio of the aryl halide compound to the catalyst may be in the range of 1:0.001 to 1:0.1, preferably 1:0.005 to 1:0.01, more preferably 1:0.005, wherein the molar weight of the catalyst is measured based on the palladium metal. Water may preferably be present in excess in the hydroxycarbonylation reaction. For example, a volume fraction of water in the reaction mixture may be at least 0.5, preferably at least 0.6, more preferably at least 0.7, with volume fraction being relative to the total volume of the reaction mixture. For example, in one embodiment, a reaction mixture is prepared by mixing 0.005 mmol of the catalyst, 1.0 mmol of iodobenzene, 2.0 mmol of KOH, and 5.0 mL of water. In one embodiment, the reaction mixture is preferably mixed in a centrifugal mixer with a rotational speed of at least 500 rpm, preferably at least 800 rpm, more preferably at least 1000 rpm, even though it can also be mixed with a spatula. In one embodiment, the reaction mixture is sonicated during the mixing.

The process for synthesizing the carboxylic acid compound further involves pressurizing the reaction chamber with carbon monoxide. The reaction chamber may be pressurized and vented at least three times, preferably at least five times with CO to ensure a volume fraction of other gaseous substances (e.g. nitrogen, oxygen, carbon dioxide, water vapor, etc.) is less than 0.001, preferably less than 0.0005, more preferably less than 0.0001. At this point, the reaction chamber can be pressurized with carbon monoxide to a pressure within the range of 80-150 psi, preferably 100-150 psi, more preferably at least 120-150 psi.

The process for synthesizing the carboxylic acid compound further involves heating the reaction chamber to react the aryl halide compound with carbon monoxide and water in the presence of the catalyst via a hydroxycarbonylation reaction to form the carboxylic acid compound. In one embodiment, the alkoxycarbonylation reaction is performed at a temperature in the range 25-200° C., preferably 80-120° C., even more preferably about 90° C. An external heat source, such as a water bath or an oil bath, an oven, or a heating mantle, may be employed to heat the reaction mixture. A duration of the reaction may range from 0.5-10 hours, preferably 2-6 hours, more preferably about 3 hours.

Additional descriptions of the processing steps of synthesizing the carboxylic acid compound via the hydroxycarbonylation reaction is similar to the processing steps of synthesizing the aryl ester compound via the alkoxycarbonylation reaction (as in the first aspect), except water is used instead of the alcohol. In one embodiment, for circumstances where water cannot be used (i.e. water does not dissolve the aryl halide compound and the base), a water soluble organic solvent is used.

DESCRIPTION OF ORGANIC SUBSTITUENTS

The term "alkyl", as used herein, unless otherwise specified, refers to a straight, branched, or cyclic hydrocarbon fragment. Non-limiting examples of such hydrocarbon fragment include methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, vinyl, ally , 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl. As used herein, the term "cyclic hydrocarbons" refers to cyclized alkyl groups. Exemplary cyclic hydrocarbon (i.e. cycloalkyl) groups include, but are not limited to, cyclopropyl, cyclobutyl, cyclopentyl, cyclohexyl, norbornyl, and adamantyl. Branched cycloalkyl groups, such as exemplary 1-methylcyclopropyl and 2-methycyclopropyl groups, are included in the definition of cycloalkyl as used in the present disclosure.

The term "cycloalkyl" as used in this disclosure refers to a cyclic alkyl having 3 to 7 carbon atoms and includes cyclopropyl, cyclobutyl, cyclopentyl, cyclohexyl, cycloheptyl. Further, "substituted cycloalkyl" may refer to cyclopropyl, cyclobutyl, cyclopentyl, cyclohexyl, or cycloheptyl substituted by at least one substituent selected from aroyl (as defined below), halogen (e.g. chlorine, bromine, fluorine or iodine), amino, nitro, hydroxy, alkyl, alkoxy (i.e. straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy including cyclopentyloxy, cyclohexyloxy and cycloheptyloxy, including phenoxy and phenoxy substituted with halo, alkyl, alkoxy, haloalkyl which means straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoromethyl, 2,3,3-trifluoropropyl, 1,1,2,2-tetrafluoroethyl, 2,2,3,3-tetrafluoropropyl.

The term "cycloalkylalkyl" as used in this disclosure refers to a straight or branched chain alkyl moiety having 1 to 8 carbon atoms that is substituted by a cycloalkyl group having 3 to 7 carbon atoms, and includes, for example, cyclopropylcarbinyl (i.e., carbinyl may also be termed methyl in this context), cyclobutylcarbinyl, cyclopentylcarbinyl, cyclohexylcarbinyl, cycloheptylmethyl, 2-cyclo-propylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, cyclohexylbutyl, 6-cyclopro-pylhexyl, 6-cyclohexylhexyl.

The term "arylalkyl" as used in this disclosure, may include those radicals in which an aryl group is attached to an alkyl group (e.g., benzyl, phenethyl, pyridylmethyl, etc.) including those alkyl groups in which a carbon atom containing group (e.g., a methylene group) has been replaced by, for example, an oxygen atom (e.g., phenoxymethyl, 2-pyridyloxymethyl, 3-(1-naphthyloxy)propyl, etc.).

The term "heteroaryl" as used in this disclosure refers to 5 to 10 membered mono- or fused-hetero-aromatic ring which has at least one hetero atom selected from nitrogen, oxygen, and sulfur, and includes, for example, 2-furyl, 3-furyl, 2-thienyl, 3-thienyl, 2-pyridyl 4-pyridyl, pyrazolyl; imidazolyl, pyrimidinyl, pyridazinyl, pyrazinyl, benzimidazolyl, quinolyl, oxazolyl, thiazolyl, indolyl. Further, "substituted heteroaryl" may refer to 5 to 10 membered mono- or fused-heteroaromatic ring which has in the ring at least one hetero atom selected from nitrogen, oxygen, and sulfur, and which ring is substituted by at least one substituent selected from halogen, amino, vitro, hydroxy, alkyl, alkoxy and haloalkyl on the above-mentioned heteroaromatic nucleus.

The term "aryl" as used in this disclosure refers to phenyl, biphenyl, naphthyl,. anthracenyl, and includes heteroaryl that can be furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl, (or its N-oxide), thienyl, pyrimidinyl (or its N-oxide), 1H-indolyl, isoquinolyl (or its N-oxide) or quinolyl (or its N-oxide). Further, the term "substituted aryl" may refer to phenyl, naphthyl, or biphenyl substituted by at least one substituent selected from aroyl (as defined below), halogen (e.g. chlorine, bromine, fluorine or iodine), amino, vitro, hydroxy, alkyl, alkoxy (i.e. straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decyloxy), cycloalkyloxy cyclopentyloxy, cyclohexyloxy and cycloheptyloxy, aryloxy including phenoxy and phenoxy substituted with halo, alkyl, alkoxy, haloalkyl which means straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3~ifluoropropyl, 4,4~ichlorobutyl, 4,4~difluorobutyl , trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl.

The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon or sulphur. Examples of such monocyclic rings include oxaziridinyl, oxiranyl, dioxiranyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has one or more oxygen atoms bonded to the ring (i.e. as ring atoms). Preferably, said atom which is bonded to the ring selected from nitrogen or sulphur. An example of a heterocyclyl substituted with one or more oxygen atoms is 1,1-dioxido-1,3-thiazolidinyl.

The term "alkylthio" as used in this disclosure refers to a divalent sulfur with alkyl occupying one of the valencies and includes the groups methylthio, ethylthio, propylthio, butylthio, pentylthio, hexylthio, octylthio.

The term "alkanoyl" as used in this disclosure refers to an alkyl group having 2 to 18 carbon atoms that is bound with a double bond to an oxygen atom. Examples of alkanoyl include, acetyl, propionyl, butyryl, isobutytyl, pivaloyl, valeryl, hexanoyl, octanoyl, lauroyl, stearoyl.

The term "aralkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimeth-ylbenzyl, 2-(4-ethylphenyl)ethyl, 3-(3-propylphenyl)propyl. Further, "substituted aralkyl" may refer to aralkyl substituted by at least one substituent selected from aroyl (as defined below), halogen (chlorine, bmmine, fluorine or iodine), amino, vitro, hydroxy, alkyl, alkoxy (which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy and decycloxy), cycloalkyloxy including cyclopentyloxy, cyclohexyloxy and cycloheptyloxy, aryloxy including phenoxy and phenoxy substituted with halo, alkyl, alkoxy, haloalkyl which means straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3~ifluoropropyl, 4,4-dichlorobutyl, 4,4-fluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl; "substituted benzyl" means benzyl substituted as in substituted aralkyl.

Examples of aroyl are benzoyl and naphthoyl, and "substituted aroyl" may refer to benzoyl naphthoyl substituted by at least one substituent including those selected from halogen, amino, vitro, hydroxy, alkoxy and haloalkyl on the benzene or naphthalene ring.

The term "heteroarylcarbonyl" as used in this disclosure refers to a heteroaryl moiety with 5 to 10 membered mono- or fused- heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus; and includes, for example, 2-oxo-1,3-dioxolan-4-ylmethyl, 2-oxo-1,3-dioxan-5-yl.

Vinyl refers to an unsaturated substituent having at least one unsaturated double bond and having the formula $CH_2=CH-$. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl.

The term "hydrocarbyl" as used herein refers to a univalent hydrocarbon group containing up to about 24 carbon atoms (i.e., a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted awl, cycloalkyl-substituted aryl, aralkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

Substituted aryl halide as used in this disclosure refers to an aryl halide in which the aryl group is a substituted aryl group where the substitution includes in addition to a halide atom, at least one other substituent included in the above definition of substituted aryl. Said substituted arylolefin refers to a product formed by a palladium-catalyzed reaction of a substituted aryl halide and an olefin as described in this disclosure. In addition, arylalkylcarboxylic acid refers to a product formed by a palladium-catalyzed reaction of an arylolefin and carbon monoxide and water. Moreover, substituted arylalkylcarboxylic acid refers to a product formed by a palladium-catalyzed reaction of a substituted arylolefin (i.e. an olefin which contains a substituted aryl as defined above) and carbon monoxide and water.

The term "substituted" may also refer to at least one hydrogen atom that is replaced with a non-hydrogen group, provided that normal valencies are maintained and that the substitution results in a stable compound. When a compound ore R group (denoted as $R^1$, $R^2$, and so forth) is noted as "optionally substituted", the substituents are selected from the exemplary group including, but not limited to, halo, hydroxy, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl, or arylakyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamido (e.g. —$SO_2NH_2$), substituted sulfonamide, nitro, cyano, carboxy, carbamyl (e.g. —$CONH_2$), substituted carbamyl (e.g. —CONHalkyl, —CONHaryl, —CONHarylalkyl or cases where there are two substituents on one nitrogen from alkyl, aryl, or arylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like. The substituents may be either unprotected, or protected as necessary, as known to those skilled in the art.

The examples below are intended to further illustrate protocols for synthesizing an aryl ester compound or an amide compound, and are not intended to limit the scope of the claims.

EXAMPLE 1

The following examples show the application of a palladium-bis(oxazoline) complex supported on Merrifield's resin as a highly active heterogeneous catalyst in the production of aryl esters and amides via alkoxycarbonylation and aminocarbonylation of various aryl iodides. The palladium heterogeneous catalysts showed an excellent stability and recycling ability. The process represents a simple and attractive method for the production of highly value-added esters and amides that should be of high interest to many chemical and petrochemicals companies.

EXAMPLE 2

The BOX ligand was prepared using an earlier published procedure [M. B. Ibrahim, B. El Ali, M. Fettouhi, L. Ouahab, Appl. Organometal. Chem,2015, 29, 400;M. B. Ibrahim, S. M. Shakil Hussain, A. Fazal, M. Fettouhi, B. El Ali, J. Coord. Chem.2015, 68:3, 432; S. M. Shakil-Hussein, M. B. Ibrahim, A. Fazal, R. Suleiman, M. Fettouhi and B. El Ali, Polyhedron, 2014, 70, 39]. A solution of 4-iodophthalonitrile (4.0 mmol) and zinc triflate (5.0 mol %, 0.2 mmol) in dried chlorobenzene (30 mL) was stirred at room temperature for 15 minutes. A solution of 2-Amino-2-methyl-1-propanol (8.0 mmol) in dry chlorobenzene (5 mL) was slowly added. The temperature was raised to 135° C. and the reaction mixture was refluxed for 24 hours. The solvent was removed using rotary evaporator. The crude product was dissolved in 30 mL of dichloromethane and extracted twice with distilled water (2×20.0 mL). The aqueous layer was then separated and the combined organic layers were dried with anhydrous sodium sulfate. The dichloromethane was removed using a rotary evaporator to obtain the impure product, which was then purified using silica gel column chromatography with dichloromethane/ether (4/1) as eluent. The product of this step is called BOX-1 having a chemical structure as shown in FIG. 1.

Figure 2:
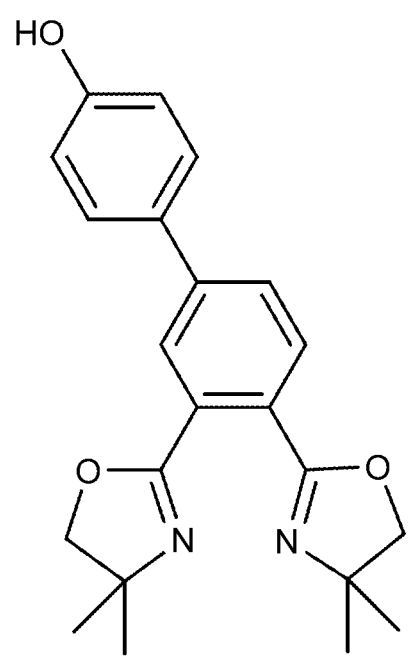
FIG. 2 is a chemical structure of a catalyst ligand (i.e. BOX-2).

BOX-1 (0.50 mmol), $PdCl_2$ (0.025 mmol, 5.0 mol %), $K_2CO_3$ (1.0 mmol, 2.0 mol equivalent), DMF (2 mL), distilled water (2 mL) and the 4-hydroxy phenylboronic acid (0.6 mmol), were added in a 10 mL round bottom flask. The mixture was stirred at 70° C. for 6 h. After completion of the reaction, the mixture was cooled down and acidified with 1M HCl. The acidified solution was extracted 3 times with Et-OAc and the combined Et-OAc extract was dried using anhydrous $MgSO_4$. The solvent was removed under reduced pressure and the product was purified by silica gel column chromatography using hexane-Et-OAc (1:9) as an eluent. The product of this step is called BOX-2 having a chemical structure as shown in FIG. 2.

Figure 3:
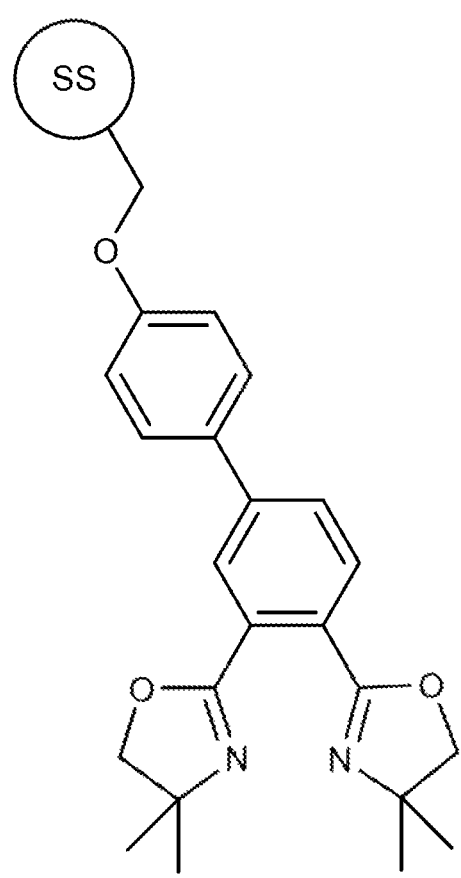
FIG. 3 is a chemical structure of a solid-supported catalyst ligand (i.e. BOX-3).

NaH (0.5 mmol) was added in one portion to a stirred solution of BOX-2 (0.30 mmol) in dry DMF in a dry flask. The mixture was stirred for 2 h at room temperature and under argon atmosphere, Merifield's resin (0.30 mmol) was added and the mixture was stirred at 90° C. for 12 h. The solid product was filtered and washed successively with methanol, water, acetone and dichloromethane. The product was dried at room temperature under vacuum [K. Hallamn, C. Moberg, Tetrahedron: Asymmetry,2001, 12, 1475]. The product of this step, which is Merrifield's resin supported bis(oxazoline) ligand, is called BOX-3 that has a chemical structure as shown in FIG. 3.

Figure 4:
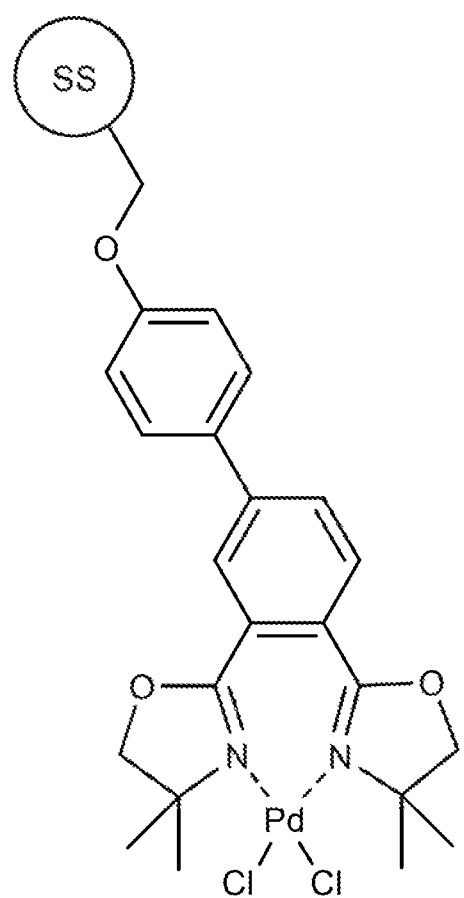
FIG. 4 is a chemical structure of a palladium solid-supported catalyst ligand (i.e. Pd-BOX catalyst).

The Merrifield's resin supported bis(oxazoline) ligand (0.3 mmol) was stirred in anhydrous ethanol for 30 min. An ethanolic solution of bis(benzonitrile) palladium(II) chloride (0.3 mmol) was added and the resulting mixture was stirred at 50° C. for 12 h. The solid product was filtered, washed thoroughly with ethanol and dried in vacuum [M. Bakherad, B. Bahramian, H. Nasr-Isfahani, A. Kievanloo, G. Sang, Chin. J. Chem.2009, 27, 353], to form the catalyst (i.e. Pd-BOX) that has a chemical structure as shown in FIG. 4.

EXAMPLE 3

A basic stainless steel autoclave equipped with a glass liner, gas inlet valve and pressure gauge was used for the reaction. The immobilized palladium catalyst (0.005 mmol based, on palladium), iodobenzene (1.0 mmol), KOH (2.0 mmol) and alcohol (5.0 mL) were added in the glass liner which was then placed in 45 mL autoclave. The autoclave was vented three times with CO and then pressurized to 100 psi CO. The mixture was heated to 100° C. and maintained at this temperature under stirring for the required time. After the reaction is complete, the mixture was cooled down to room temperature and the excess of CO was released under fume hood. The catalyst was carefully separated from the product. The product mixture was immediately analyzed with GC and GC-MS. The recovered catalyst was carefully washed and dried wider vacuum in a desiccator before the next use.

EXAMPLE 4

A basic stainless steel autoclave equipped with a glass liner, gas inlet valve and pressure gauge was used for the reaction. The immobilized palladium catalyst (0.005 mmol based on palladium), iodobenzene (1.0 mmol), amine (2.0 mmol), triethylamine (3.0 mmol), and acetonitrile (5.0 mL) were added to the glass liner. The glass liner was then placed in 45 mL autoclave. The autoclave was vented three times with CO and then pressurized to 100 psi CO. The mixture was heated to 120° C. and maintained at this temperature under stirring for the required time. After the reaction is complete, the mixture was cooled down to room temperature and the excess of CO was released under fume hood. The catalyst was carefully separated from the product. The product mixture was immediately analyzed with GC and GC-MS. The recovered catalyst was carefully washed and dried under vacuum in a desiccator before the next use.

EXAMPLE 5

Palladium-catalyzed alkoxycarbonylation reaction of aryl halides is a versatile reaction for the synthesis of various aromatic carboxylic acids and their derivatives. The reaction is of synthetic value due to the exceptionally low cost of carbon monoxide and from the diversity of aromatic esters that can be achieved by selecting the proper alcohol. In our investigation, we have chosen the methoxycarbonylation of iodobenzene using Pd-BOX complex supported on Merrifield's resin as a catalyst. We have studied the influence of various reaction parameters including temperature base, solvent, and type of palladium catalyst.

Figure 5A:
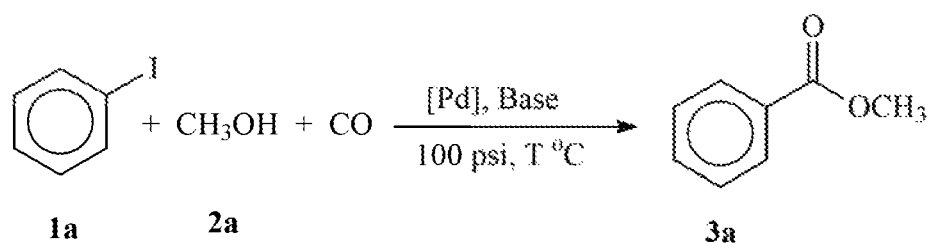
FIG. 5A is a scheme of methoxycarbonylation reaction of iodobenzene with methanol in the presence of the Pd-BOX catalyst.

A preliminary alkoxycarbonylation reaction of an aryl halide (e.g. iodobenzene) with methanol in the presence of the Pd-BOX is shown in FIG. 5A. Accordingly, iodobenzene (1a) with methanol (2a) using the catalytic system ([Pd]/ KOH / CH$_3$OH / 70° C.) (Table 1, entry 1) yielded 50% of methyl benzoate (3a) after 3 h reaction. The catalytic activity was found to be highly temperature dependent. The yield of methylbenzoate increased significantly from 50% to 85% when the temperature was raised from 70° C. (Table 1, entry 1) to 100° C. (Table 1, entry 2) and to 90% yield at 110° C. (Table 1, entry 3). Full conversion of iodobenzene and almost quantitative yield of the ester was obtained on raising the temperature to 120° C. (Table 1, entry 4). The selectivity was not affected by changing the reaction temperature.

We further screened various bases using the temperature. Potassium hydroxide gave excellent yield (99%) of the product (Table 1, entry 4). Similarly, full conversion and almost quantitative yield was obtained with NaOH (Table 1, entry 5). Potassium carbonate gave 96% of the methyl benzoate (Table 1, entry 6). The use of an organic base such as triethylamine resulted in an excellent yield of the required ester (93%) (Table 1, entry 7). We have then studied the reaction using acetonitrile as a solvent and methanol as a nucleophile (Table 1, entry 8), where comparable excellent yield of the ester was achieved.

The effect of the type of palladium catalyst on the methoxycarbonylation of iodobenzene was investigated. No product was obtained in the absence of palladium catalyst (Table 1, entry 9). The supported palladium-bis(oxazoline) complex supported on Merrifield's resin (Table 1, entry 4) yielded a full conversion and 100% selectivity in favor of the methyl benzoate. We have further compared the catalytic activity of our newly prepared palladium-bis(oxazoline) complex supported on Merrifield's resin with some commercially available palladium complexes and salts such as Pd(PPh$_3$)$_2$Cl$_2$ (Table 1, entry 10) (96%), Pd(PhCN)$_2$Cl$_2$ (Table 1, entry 11) (99%) and Pd(OAc)$_2$ (Table 1, entry 12) (95%). Interestingly, the palladium salts and complexes were similar in activity to our newly prepared supported palladium-bis(oxazoline) complex. However, the newly prepared palladium-bis(oxazoline) complex supported on Merrifield's resin possess the potential of being recycled and reused several times for the same or reactions. Consequently, the supported palladium-bis(oxazoline) complex possess higher turnover number (TON) and turnover frequency (TOF) than most commercially available palladium complexes and salts.

TABLE 1

Palladium-Bis(Oxazoline) supported on Merrifield's resin catalyzed methoxycarbonylation of iodobenzene (1a).[a]

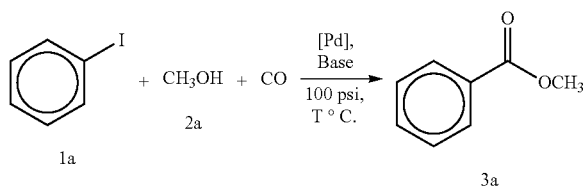

| Entry | Pd-Complex | Solvent (5 mL) | Base | T (° C.) | Yield 3a (%)[b] |
|---|---|---|---|---|---|
| 1 | Pd-BOX | Neat CH$_3$OH | KOH | 70 | 50 |
| 2 | Pd-BOX | Neat CH$_3$OH | KOH | 100 | 85 |
| 3 | Pd-BOX | Neat CH$_3$OH | KOH | 110 | 90 |
| 4 | Pd-BOX | Neat CH$_3$OH | KOH | 120 | 99 |
| 5 | Pd-BOX | Neat CH$_3$OH | NaOH | 120 | 99 |
| 6 | Pd-BOX | Neat CH$_3$OH | K$_2$CO$_3$ | 120 | 96 |
| 7 | Pd-BOX | Neat CH$_3$OH | Et$_3$N | 120 | 93 |
| 8 | Pd-BOX | CH$_3$CN/CH$_3$OH | KOH | 120 | 99 |
| 9 | — | Neat CH$_3$OH | KOH | 120 | Traces |
| 10 | Pd(PPh$_3$)$_2$Cl$_2$ | Neat CH$_3$OH | KOH | 120 | 96 |

TABLE 1-continued

Palladium-Bis(Oxazoline) supported on Merrifield's resin catalyzed methoxycarbonylation of iodobenzene (1a).[a]

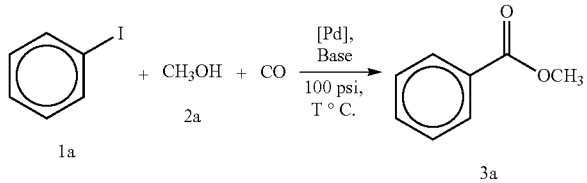

| Entry | Pd-Complex | Solvent (5 mL) | Base | T (° C.) | Yield 3a (%)[b] |
|---|---|---|---|---|---|
| 11 | Pd(PhCN)$_2$Cl$_2$ | Neat CH$_3$OH | KOH | 120 | 99 |
| 12 | Pd(OAc)$_2$ | Neat CH$_3$OH | KOH | 120 | 95 |

[a]Reaction conditions: [Pd] (0.0050 mmol), iodobenzene (1.0 mmol), solvent (5.0 mL), base (2.0 mmol). CO (100 psi), 3 h.
[b]GC Yield.

EXAMPLE 6

Figure 6:
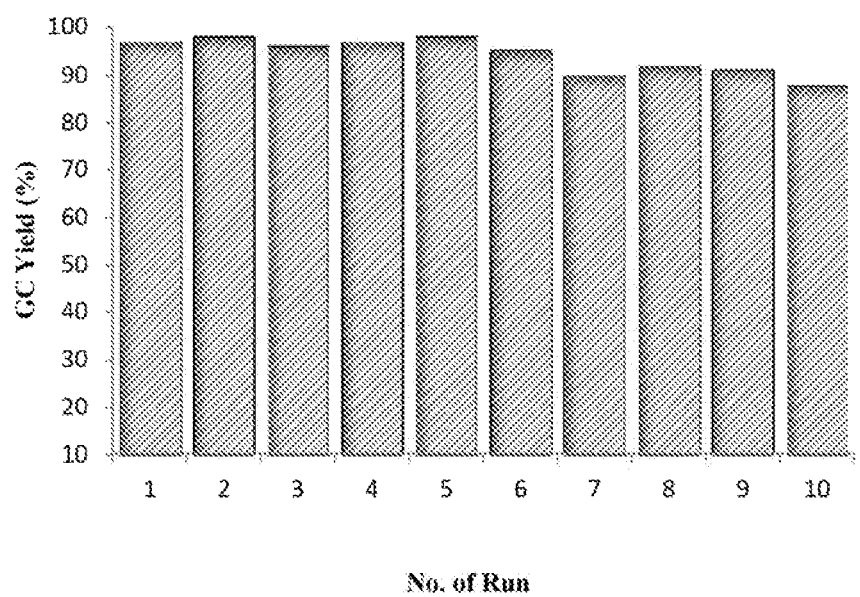
FIG. 6 represents a yield of formation of methyl benzoate via a methoxycarbonylation reaction of iodobenzene with methanol in the presence of the Pd-BOX catalyst and after recycling the Pd-BOX catalyst. It also reveals a recycling ability of the Pd-BOX catalyst.

The recycling, ability of the new palladium-bis(oxazoline) catalysts supported on Merrifield's resin) was investigated in the methoxycarbonylation reaction of iodobenzene at 100 psi CO pressure and a temperature of 100° C. for 6 h. The result of the recycling experiment is presented in FIG. 6. Remarkably, the supported catalyst could be recycled up to ten times devoid of substantial loss in its catalytic activity. The TON of the supported catalyst was estimated for the 10 cycles as 1884, while the TOF was estimated as 314/h. In order to confirm the effectiveness and the high activity realized with the supported catalyst, we have conducted experiment with the amount of iodobenzene equal to the total amount used in all the ten cycles (10.0 mmol) using the same quantity of supported palladium-bis(oxazoline) catalyst (0.005 mmol) (substrate to catalyst ratio equals to 2000). Excellent yield of methyl benzoate (95%) was recorded. Similarly, the TON of the supported palladium-bis(oxazoline) catalysts in the later experiment was estimated as 1860, while the TOF was estimated as 310/h.

EXAMPLE 7

Figure 5B:
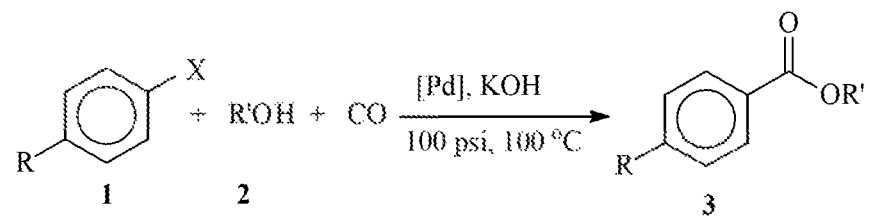
FIG. 5B is a general alkoxycarbonylation reaction scheme of an aryl halide with an alcohol in the presence of the Pd-BOX catalyst, wherein X is a halogen.

The excellent recycling ability realized with the new supported palladium-bis(oxazoline) complex in the methoxycarbonylation of iodobenzene encouraged us to study the scope of the new catalytic system and to examine its recycling ability in the alkoxycarbonylation reaction of a broad range of substrates using a CO pressure of 100 psi and KOH as a base. Thus, the alkoxycarbonylation of iodobenzene with various alcohols including aliphatic (primary, secondary and tertiary aliphatic alcohols) as well as aromatic alcohols were studied (Table 2). A general scheme of alkoxycarbonylation reaction of an aryl halide with alcohol in the presence of the Pd-BOX is shown in FIG. 5B. The catalyst used in the first example (Table 2, entry 1) was carefully separated, washed with methanol and dried in an oven at 100° C. for 2 h. The recovered catalyst could be again used in the alkoxycarbonylation of aryl iodide if the same cleaning and dying procedures after each reaction are applied. However, a fresh catalyst was used for the study with various substrates. All the alcohols studied gave excellent conversions, and in some cases the corresponding esters were isolated in excellent yields. Primary aliphatic alcohols (Table 2, entries 1-3) reacted smoothly to yield the corresponding aromatic ester. The reactivity of primary alcohols was not affected by the length of the carbon chain. Secondary and tertiary aliphatic alcohols (Table 2, entries 4 and 5), however, were relatively less reactive compared to the primary alcohols and therefore longer reaction time was necessary to achieve a full conversion of their alkoxycarbonylation reactions. In the alkoxycarbonylation reactions, the alcohol served as both nucleophile and solvent for the reaction. The alkoxycarbonylation reaction of iodobenzene with phenol was carried out using acetonitrile as a solvent (Table 2, entry 7).

The impact of electronic effect of various aryl iodides on their reactivity in the carbonylation reactions was also studied. Both activated and deactivated aryl iodides worked effectively to lead to the corresponding aromatic esters. The presence of a deactivating group on the aryl iodide enhanced its reactivity and the corresponding ester was isolated in excellent yield (94%) (Table 2, entry 9). Similarly, 4-iodoanisole reacted smoothly to yield methyl 4-methoxybenzoate (Table 2, entry 10) in high yields. The methoxycarbonylation of 1,4-thiodobenzene was also successful and yields 92% of dimethylbenzene-1,4-dicarboxylate (Table 2, entry 11).

TABLE 2
Alkoxycarbonylation of aryl iodide by the Pd-BOX Supported on Merrifield's Resin as a catalyst.[a]
| Entry | Aryl Iodide 1a-d | Alcohol 2a-h | Product (ester) 3a-k | Time (h) | Yield (%)[b,c] |
|---|---|---|---|---|---|
| 1 |  1a | CH$_3$OH 2a | 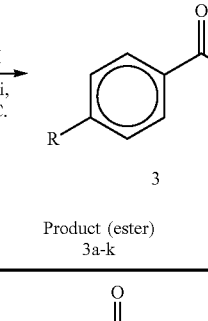 3a | 6 | 99 |
| 2 | 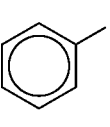 1a |  2b | 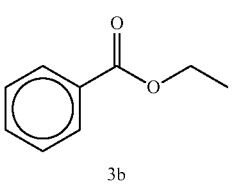 3b | 6 | 99 |
| 3 | 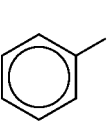 1a | 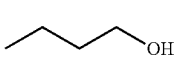 2c | 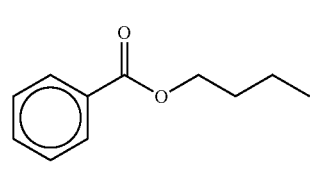 3c | 6 | 96 |
| 4 | 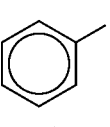 1a | 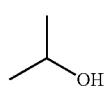 2d | 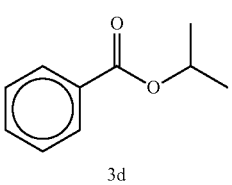 3d | 12 | 95 |
| 5 | 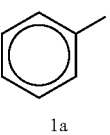 1a |  2e | 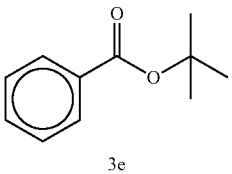 3e | 12 | 99 [92] |
| 6 |  1a | 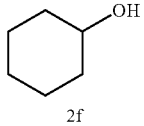 2f | 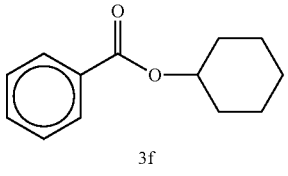 3f | 12 | 99 [93] |
| 7 | 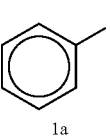 1a | 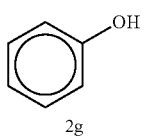 2g | 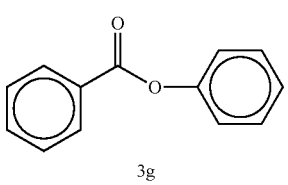 3g | 6 | 99 [95] |

TABLE 2-continued

Alkoxycarbonylation of aryl iodide by the Pd-BOX Supported on Merrifield's Resin as a catalyst.[a]

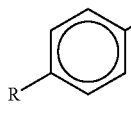

| Entry | Aryl Iodide 1a-d | Alcohol 2a-h | Product (ester) 3a-k | Time (h) | Yield (%)[b,c] |
|---|---|---|---|---|---|
| 8 | 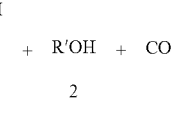 1a | 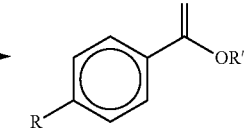 2h | 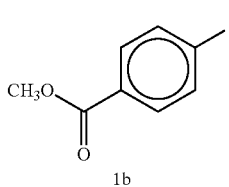 3h | 6 | 99 [92] |
| 9 |  1b | CH$_3$OH 2a | 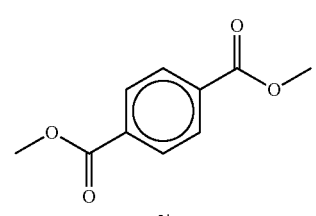 3i | 6 | 99 [94] |
| 10 | 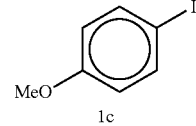 1c | CH$_3$OH 2a |  3j | 6 | 96 [90] |
| 11 | 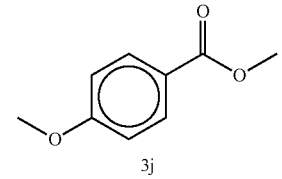 1d | CH$_3$OH 2a | 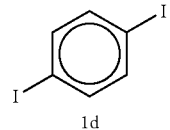 3k | 12 | 99 [92] |

[a]Reaction conditions: [Pd] (0.005 mmol), aryl iodide (1.0 mmol), alcohol (5 mL), KOH (2.00 mmol), CO (100 psi), 100° C.
[b]GC yield.
[c]Isolated yields are given in brackets.
[d]Phenol (2.0 mmol), CH$_3$CN (5.0 mL), 120° C.

EXAMPLE 8

Figure 7A:
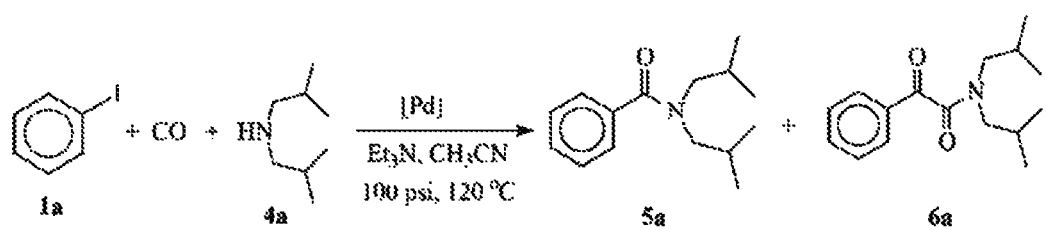
FIG. 7A is a scheme of aminocarbonylation reaction of iodobenzene with diisobutylamine in the presence of the Pd-BOX catalyst.
Figure 7B:
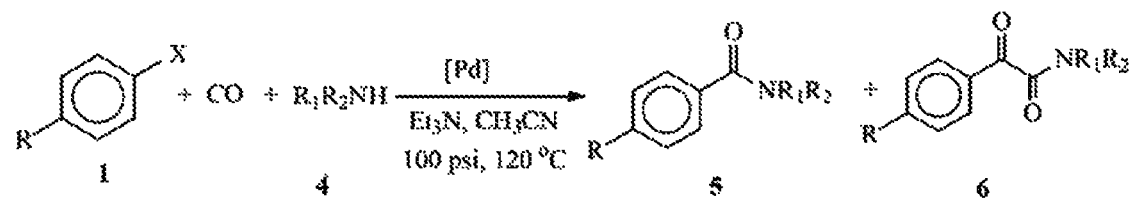
FIG. 7B is a general aminocarbonylation reaction scheme of an an halide with amine in the presence of the Pd-BOX catalyst, wherein X is a halogen.

Palladium-catalyzed aminocarbonylation of aryl halides is a widely used methodology in the synthesis of carboxamides from easily accessible starting materials. Various amides including those with bulky N-substitutions can easily be accessed by selecting the proper aryl halide and amine. We have tested the catalytic activity of the new supported palladium-bis(oxazoline) complex in the aminocarbonylation of aryl iodides. A reaction scheme of iodobenzene with diisobutylamine in the presence of the Pd-BOX is shown in FIG. 7A. Additionally, various amines were considered in this reaction. A general scheme of aminocarbonylation reactions of aryl halide with amine in the presence of the Pd-BOX is shown FIG. 7B.

The recycling ability of the new palladium-bis(oxazoline) complex supported on Merrifield's resin was also investigated in the aminocarbonylation reaction of iodobenzene with diisobutylamine (DIBA) in the presence of trimethylamine as a base at 100 psi CO pressure and a temperature of 120° C. for 6 h. The results of the recycling experiments are presented on Table 3. The supported complex was recycled up to six times without showing significant loss in their catalytic activities. However, a drop in activity to 61% conversion of iodobenzene was observed with the supported catalyst during the seventh cycle.

TABLE 3

Aminocarbonylation of iodobenzene with diisobutylamine (DIBA).
Recycling Ability of Pd-BOX supported on Merrifield's resin.[a]

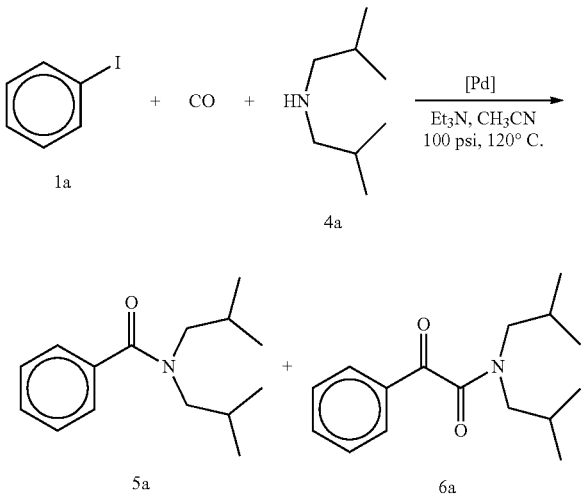

| Cycle | Conversion[b] % | Product Distribution[c] % | |
|---|---|---|---|
| | | 5a | 6a |
| 1 | 99 | 96 | 4 |
| 2 | 99 | 95 | 5 |
| 3 | 99 | 96 | 4 |
| 4 | 92 | 96 | 4 |
| 5 | 88 | 96 | 4 |
| 6 | 85 | 96 | 4 |
| 7 | 61 | 95 | 5 |

[a]Reaction conditions: [Pd] (0.005 mmol), iodobenzene (1.0 mmol), DIBA (2.0 mmol), Et$_3$N (3.0 mmol), acetonitrile (5.0 mL), CO (200 psi), 120° C., 6 h
[b]Determined by GC based on iodobenzene.
[c]Determined by GC.

EXAMPLE 9

We have extended the scope of the aminocarbonylation reaction by considering various amines including primary and secondary amines as nucleophiles and various aryl iodides (Table 4, entries 1-7) as substrates. The rate of the aminocarbonylation reaction was found to depend highly on the type of the amine employed. For instance, secondary amines such as diisobutylamine and dicyclohexylamine reacted smoothly with iodobenzene (Table 4, entries 1 and 2). The reaction of iodobenzene with diisobutylamine yielded the corresponding carboxamide (96%) and a keto-carboxamide (4%). However, the reaction of iodobenzene with dicyclohexylamine yielded the carboxamide as the only product. The aminocarbonylation of iodobenzene with amine as nucleophile was also successful and yielded selectively N-phenylbenzamide as sole product (Table 4, entry 3). The catalyst system also give excellent conversions in the aminocarbonylation of iodobenzene with primary amines as nucleophiles (Table 4, entries 4 and 5). However, in contrast to secondary amines, primary amines show relatively poor selectivity and a mixture of carbonylation and double carbonylation products were obtained.

The effect of substituent on the aryl iodide was also investigated in the aminocarbonylation reaction. Interestingly, the supported palladium-bis(oxazoline) complexes were highly active in the aminocarbonylation reactions of both activated and unactivated aryl iodides. For instance, the aminocarbonylation of 4-iodoanisole (1d) and methyl 4-iodobenzoate (1c) with diisobutylamine were achieved to give excellent conversions and very high selectivities in the carboxamides (Table 4, entries 6 and 7).

TABLE 4
Aminocarbonylation of aryl iodides using Pd-BOX supported on Merrifield's Resin as Catalyst.
| Entry | Aryl halide 1 a-d | Amine 4a-c | Conversion[b] % | Product Distribution[c] % | |
|---|---|---|---|---|---|
| | | | | 5 | 6 |
| 1 | 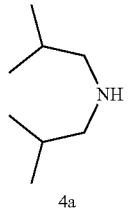 1a |  4a | 99 | 96 | 4 |
| 2 | 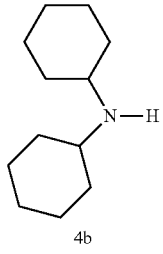 1a |  4b | 99 | 100 | 0 |
| 3 | 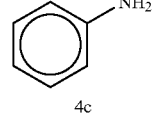 1a | 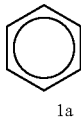 4c | 99 | 100 | 0 |
| 4 | 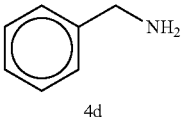 1a |  4d | 99 | 40 | 35 |
| 5 | 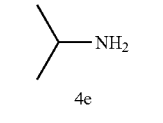 1a | 4e | 99 | 38 | 30 |

TABLE 4-continued

Aminocarbonylation of aryl iodides using Pd-BOX supported on Merrifield's Resin as Catalyst.

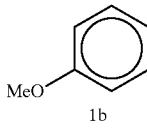

| Entry | Aryl halide 1 a-d | Amine 4a-c | Converstion[b] % | Product Distribution[c] % | |
|---|---|---|---|---|---|
| | | | | 5 | 6 |
| 6 | 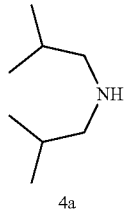 1b | 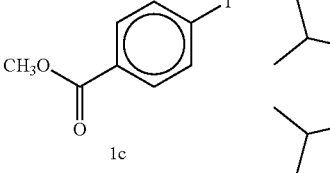 4a | 99 | 96 | 4 |
| 7 | 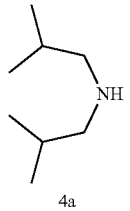 1c | 4a | 99 | 93 | 7 |
| 8 | 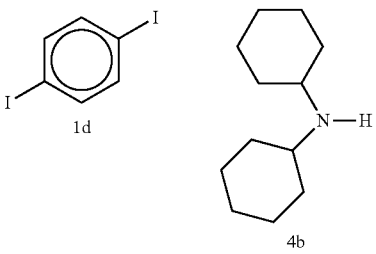 1d | 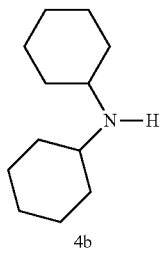 4b | 99 | 100 | 0 |

[a]Reaction conditions: Pd-BOX (0.005 mmol), Aryliodide (1.0 mmol), amine (2.0 mmol), Et₃N (3.00 mmol), CO (100 psi), 120° C., 6 h
[b]Percent converstion determined by GC based on aryl iodide.
[c]Determined by GC.

EXAMPLE 10

The ability to reuse the supported palladium-bis(oxazoline) complex several times and in various reactions without significant loss in their catalytic activities demonstrates their high stabilities. The interesting results realized with the supported catalysts urged us to carry out further investigations to asses any change in the physical and chemical structures of the used catalysts in comparison with the unused complexes. The recovered catalysts from all the two applications were analyzed with Fourier Transform Infrared Spectroscopy (FT-IR), X-Ray Photoelectron Spectroscopy (XPS) and Inductively Coupled Plasma—Mass Spectrometry (ICP-MS) techniques.

Figure 8A:
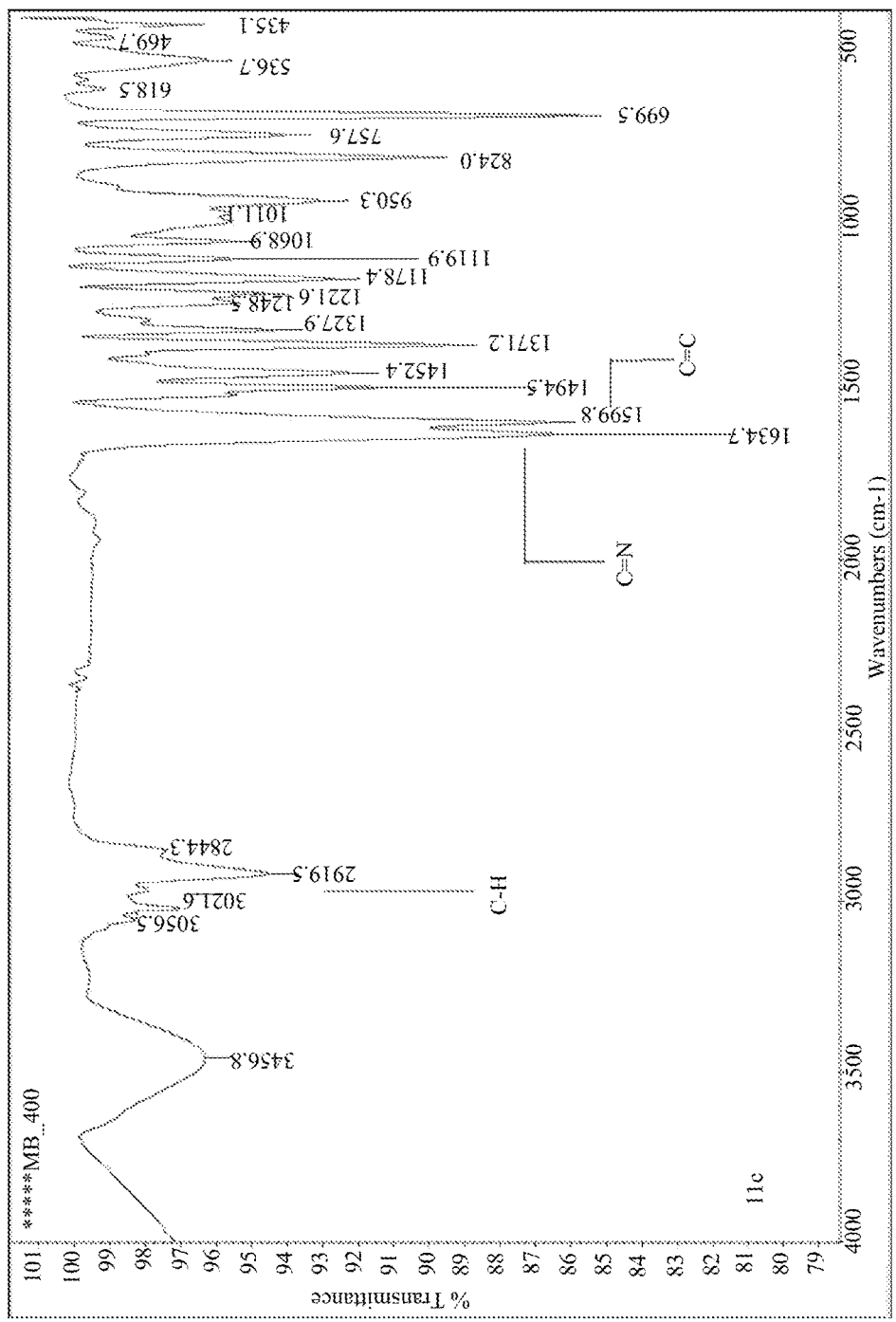
FIG. 8A is a FTIR spectrum of the Pd-BOX catalyst before being used in a carbonylation reaction.
Figure 8B:
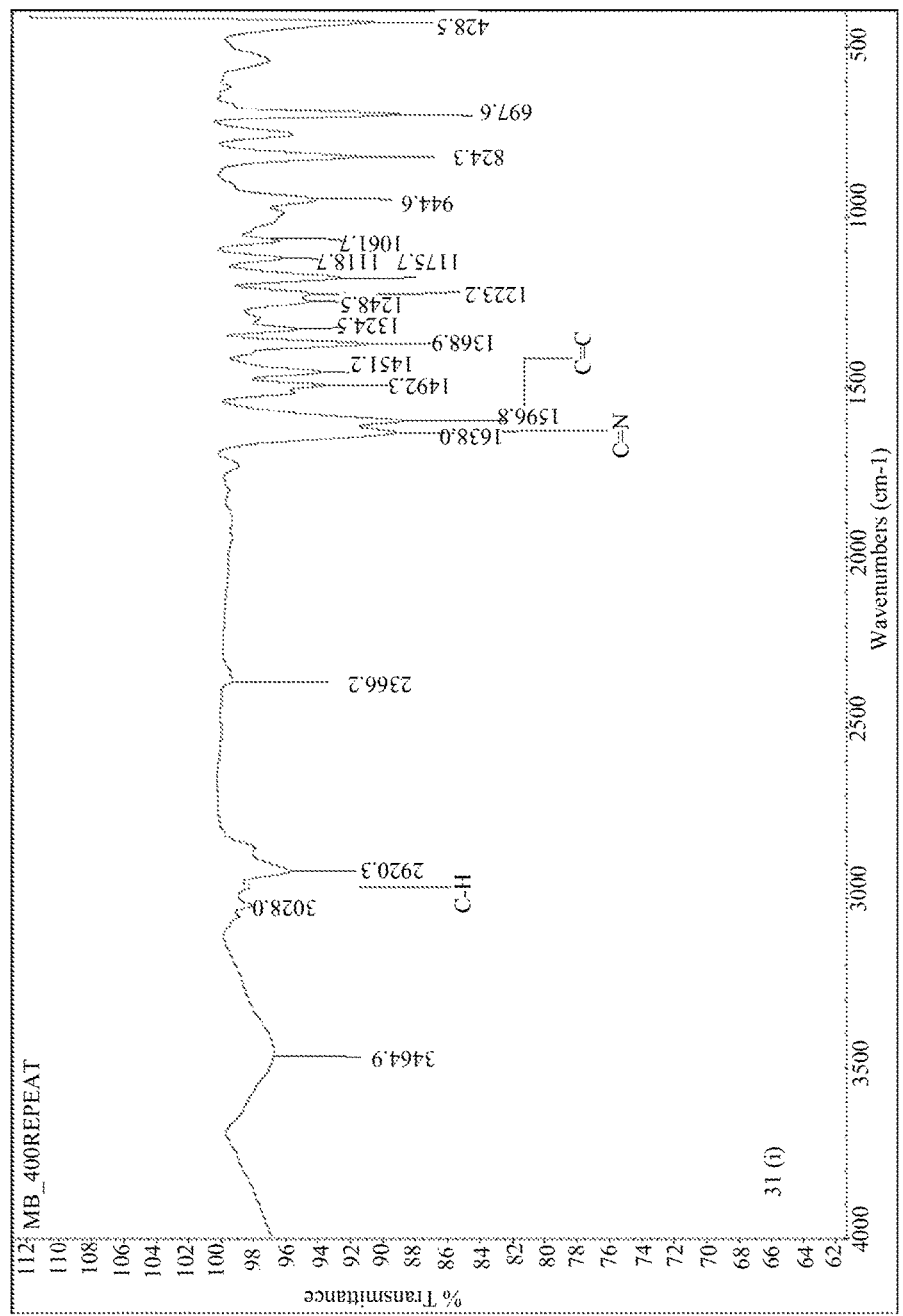
FIG. 8B is a FTIR spectrum of the Pd-BOX catalyst after being used and recovered from an alkoxycarbonylation reaction.

The recovered palladium-bis(oxazoline) catalyst was washed successively with distilled water, acetone and methanol. The catalyst was then dried, in an oven at 100° C. prior to analysis. The dried catalyst was pressed into disc with KBr and analyzed using FT-IR. The FT-IR spectrum for the recovered Merrifield's resin supported palladium-bis (oxazoline) catalysts (as shown in FIG. 8B) was found to be similar with the spectrum of the unused catalyst (as shown in FIG. 8A).

The percentage of palladium on the supported catalyst recovered after the tenth cycle of the alkoxycarbonylation reaction were determined using ICP-MS and were found to be 6.0%. Whereas, the amount of palladium on the supported catalyst recovered after the seventh cycle of the aminocarbonylation reaction was estimated as 5.1%.

These results indicate that the amount of palladium on the supported catalyst recovered from alkoxycarbonylation reactions are similar to the amount of palladium in the unused catalyst and could be the reason for the high recycling ability observed in the alkoxycarbonylation reaction.

On the other hand, the amount of palladium on the supported catalyst recovered from aminocarbonylation reaction was much less than the amount of palladium on the unused supported complex (there is 24% loss of palladium). This could be the reasons for the decrease in the catalytic activity observed in the later cycles of the aminocarbonylation experiments.

The XPS studies of the supported palladium-bis(oxazoline) recovered after the tenth cycle of the alkoxycarbonylation reaction show that, the oxidation state of palladium remains unchanged after the catalytic application. Similar to the unused supported catalyst, the 3d spectrum resolved into $3d^{5/2}$ and $3d_{3/2}$ spin orbit pairs with binding enemies of 334.88 eV and 339.98 eV, respectively [Yeap, H. N; Mian, W.; Hong, H.; Christina, L. L. C. *Chem. Commun.*, 2009, 5530; Takacs, A.; Abreu, A. R.; Peixoto, A. F.; Pereira, M.; Kollar, L. *Synth. Commun.* 2009, 39, 1534].

EXAMPLE 11

The main objective of supporting a homogeneous catalyst is to enable its easy separation from the product and to minimize the level of contamination caused by the toxic metal. The possible palladium leaching into the product was analyzed using ICP-MS. After the tenth cycle of the alkoxycarbonylation and the seventh cycle of the, aminocarbonylation, the products of each reaction were combined in separate containers. Samples were taken from each reaction for the analysis. The samples were digested using concentrated nitric acid. The solutions were then analyzed with ICP-MS technique.

The results of the ICP-MS analysis show that the concentration of palladium in the alkoxycarbonylation product is 2.0 ppb. This means that less than 0.1% of the total palladium on the supported complex was leached into the solution. On the other hand, the amount of palladium that leached into the solution during the aminocarbonylation reaction was 195.0 ppb. This amount was estimated as 3.4% of the total palladium on the supported catalyst. These results clearly show that the palladium leaching during aminocarbonylation reaction was significantly higher than the alkoxycarbonylation reaction, which explains the reason for the relatively lower recycling ability encountered during the aminocarbonylation reaction as compared to the alkoxycarbonylation reaction. The higher leaching of palladium observed with the aminocarbonylation reaction could be attributed to the coordination of palladium to the amine (either trimethylamine base or the amine nucleophile). This results in the formation of homogeneous complexes that are highly soluble in the liquid phase [Ji, Y.; Jain, S.; Davis, R. J. *J. Phys. Chem. B*, 2005, 109, 17232].

EXAMPLE 12

The esters and amides reported in this invention and prepared using our invented palladium heterogeneous catalyst system could be of high interest to most petrochemical and chemical feedstocks companies.

The invention claimed is:

1. A process for synthesizing an aryl ester compound, comprising:

mixing an aryl halide compound, an alcohol, a base, and a catalyst in a reaction chamber;

wherein the aryl halide has the following formula B:

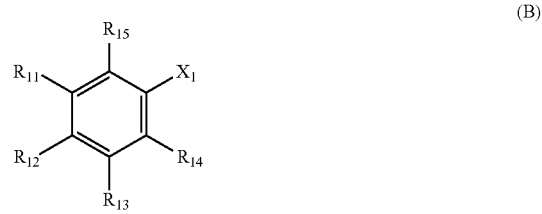

wherein $R_{11}$-$R_{15}$ are each independently a hydrogen, an alkyl, a cycloalkyl, an arylalkyl, a heteroaryl, an aryl, a heterocyclyl, an alkanoyl, an aroyl, a heteroarylcarbonyl, or a vinyl, and $X_1$ is a halogen selected from the group consisting of chlorine, bromine, and iodine, pressurizing the reaction chamber with carbon monoxide; and heating the reaction chamber to react the aryl halide compound with carbon monoxide and the alcohol in the presence of the catalyst via an alkoxycarbonylation reaction to form the aryl ester compound of formula (A),

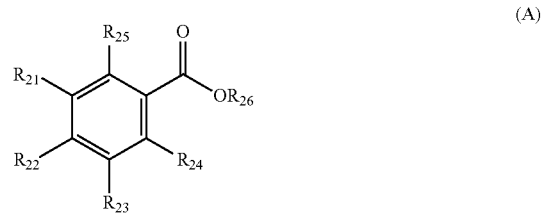

wherein $R_{21}$-$R_{25}$ are each independently an alkyl, a cycloalkyl, an arylalkyl, a heteroaryl, an aryl, a heterocyclyl, an alkanoyl, an aroyl, a heteroarylcarbonyl, or a vinyl, and $R_{26}$ is an alkyl, a cycloalkyl, an arylalkyl, an aryl, or a heterocyclyl, wherein the catalyst has a structure of formula (I):

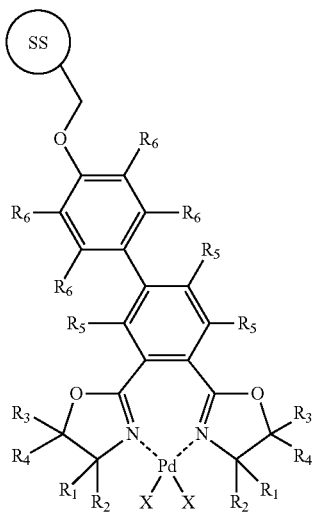

(I)

wherein $R_1$, $R_2$, $R_3$, $R_4$, $R_5$, and $R_6$ are independently a hydrogen, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted aralkyl, an optionally substituted heteroarylcarbonyl, an optionally substituted hydrocarbyl, an optionally substituted aryl halide, an optionally substituted arylolefin, an optionally substituted arylalkylcarboxylic acid, an optionally substituted benzyl, or an optionally substituted vinyl, SS is a solid support, and X is selected from the group consisting of Cl, F, Br, I, OAc, and OTf.

2. The process of claim 1, wherein the catalyst has a structure of formula (II):

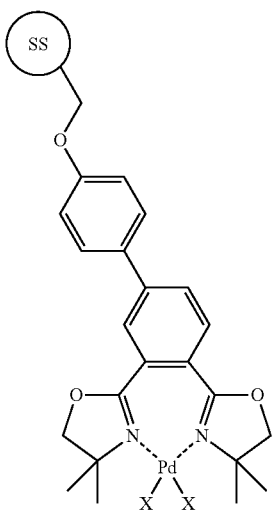

(II)

wherein SS is a solid support, and X is selected from the group consisting of Cl, F, Br, I, OAc, and OTf.

3. The process of claim 1, wherein the catalyst has a structure of formula (II):

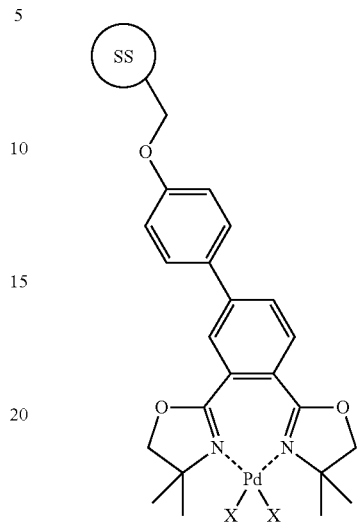

(II)

wherein SS is a Merrifield resin, and X is selected from the group consisting of Cl, F, Br, I, OAc, and OTf.

4. The process of claim 1, wherein the catalyst has a structure of formula (III):

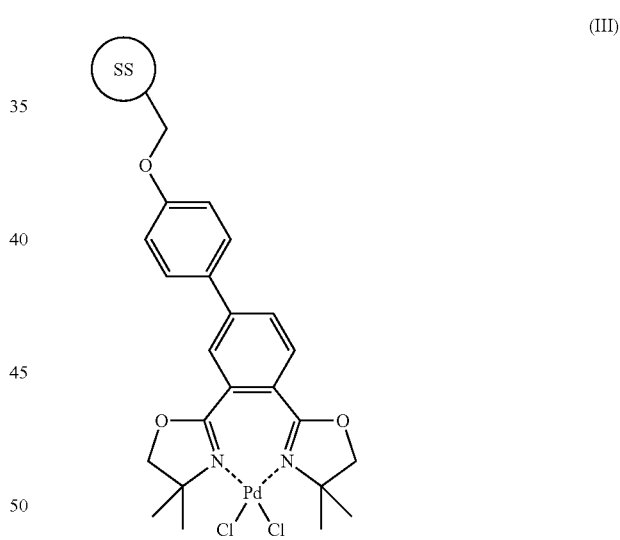

(III)

wherein SS is a Merrifield resin.

5. The process of claim 1, wherein the catalyst is in the form of spherical particles having an average diameter within the range of 1-50 nm.

6. The process of claim 1, further comprising:
separating the catalyst from the aryl ester compound; and
recycling the catalyst,
wherein the catalyst loses less than 5 wt % of the palladium metal after at least 10 cycles.

7. The process of claim 6, wherein a turnover number of the catalyst in the alkoxycarbonylation reaction after at least 10 cycles is within the range of 1,800 to 10,000.

8. The process of claim 6, wherein a turnover frequency of the catalyst in the alkoxycarbonylation reaction after at least 10 cycles is within the range of 300-2,000 per hour.

9. The process of claim 1, wherein the alkoxycarbonylation reaction is conducted at a temperature in the range 25-200° C., and a pressure in the range of 80-150 psi.

10. The process of claim 9, wherein a formation yield of the aryl ester compound is at least 80%, with the formation yield being relative to an initial molar weight of the aryl halide compound.

11. The process of claim 1, wherein the base is at least one selected from the group consisting of an alkali metal hydroxide, an alkali metal carbonate, and an amine.

12. The process of claim 1, wherein the aryl halide compound is a limiting reactant in the alkoxycarbonylation reaction.

\* \* \* \* \*